(12) United States Patent
Okamoto et al.

(10) Patent No.: US 10,912,458 B2
(45) Date of Patent: Feb. 9, 2021

(54) OPHTHALMIC APPARATUS

(71) Applicant: Tomey Corporation, Nagoya (JP)

(72) Inventors: Keiichiro Okamoto, Nagoya (JP);
Takashi Kamo, Nagoya (JP); Tomoki Hori, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 141 days.

(21) Appl. No.: 15/935,396

(22) Filed: Mar. 26, 2018

(65) Prior Publication Data

US 2018/0279872 A1 Oct. 4, 2018

(30) Foreign Application Priority Data

Mar. 28, 2017 (JP) .................................. 2017-063682

(51) Int. Cl.
| | |
|---|---|
| *A61B 3/117* | (2006.01) |
| *A61B 3/12* | (2006.01) |
| *A61B 3/13* | (2006.01) |
| *A61B 3/10* | (2006.01) |

(52) U.S. Cl.
CPC .............. *A61B 3/117* (2013.01); *A61B 3/102* (2013.01)

(58) Field of Classification Search
CPC ......... A61B 3/117; A61B 3/1173; A61B 3/12; A61B 3/13
See application file for complete search history.

(56) References Cited

U.S. PATENT DOCUMENTS

| | | |
|---|---|---|
| 8,690,328 B1 | 4/2014 | Chong |
| 2012/0083667 A1 | 4/2012 | Isogai et al. |
| 2012/0200859 A1 | 8/2012 | Breitenstein et al. |
| 2013/0100407 A1 | 4/2013 | Iwanaga et al. |
| 2014/0125951 A1 | 5/2014 | Eom et al. |
| 2015/0085253 A1 | 3/2015 | Walsh et al. |
| 2017/0245756 A1 | 8/2017 | Hayashi et al. |

FOREIGN PATENT DOCUMENTS

| | | |
|---|---|---|
| JP | 2014-138904 A | 7/2014 |
| JP | 2016-028682 A | 3/2016 |
| JP | 2016-077774 A | 5/2016 |
| JP | 2016-202371 A | 12/2016 |
| JP | 2017-502817 A | 1/2017 |
| WO | 2015/121756 A2 | 8/2015 |

*Primary Examiner* — Jack Dinh
(74) *Attorney, Agent, or Firm* — Shumaker, Loop & Kendrick, LLP

(57) ABSTRACT

A ophthalmic apparatus may include: a first light source configured to output first light to be irradiated to an anterior segment of a subject eye; and a second light source configured to output second light to be irradiated to a retina of the subject eye. The apparatus may be configured capable of executing a first examination using the first light reflected from the anterior segment and a second examination using the second light reflected from the retina. A wavelength of the second light outputted from the second light source may be smaller than a wavelength of the first light outputted from the first light source.

8 Claims, 18 Drawing Sheets

Fourier Transform

⬇ Acquire OCT (B-Scan) Data

A-Scan Measurement

Fourier Transform

A-Scan × n Lines

Acquire OCT (B-Scan) Data

OPHTHALMIC APPARATUS

TECHNICAL FIELD

The technique disclosed herein relates to an ophthalmic apparatus. More specifically, it relates to an ophthalmic apparatus configured capable of executing plural types of measurements on a subject eye.

BACKGROUND ART

An ophthalmic apparatus for measuring shapes and refractions of respective portions of a subject eye (such as an anterior segment and a retina) is being developed. Diagnosis on disorders in the subject eye and a visual function examination thereof can accurately be performed by making a comprehensive determination based on the shapes and refractions of the respective portions of the subject eye. In order to do so, plural types of measurements for each portion of the subject eye and an entirety of the subject eye are necessary, so a single ophthalmic apparatus capable of performing plural types of measurements is being developed. For example, Japanese Patent Application Publication No. 2016-77774 describes an ophthalmic apparatus that measures a cornea shape, a refraction, and an eye axial length of the subject eye. The ophthalmic apparatus of Japanese Patent Application Publication No. 2016-77774 measures a shape of an anterior surface of the cornea using a kerato measurement ring, and measures the eye axial length using optical coherence. Further, Japanese Patent Application Publication No. 2017-502817 describes an ophthalmic apparatus that measures the anterior segment and the retina using an optical coherence tomography (Optical Coherence Tomography: OCT). The ophthalmic apparatus of Japanese Patent Application Publication No. 2017-502817 splits light outputted from a single light source into two light beams having different wavelengths using a beam splitter. One of the split light beams is used for an anterior segment OCT measurement, and the other is used for a retinal OCT measurement.

SUMMARY

In the conventional ophthalmic apparatuses, the plural types of measurements were facilitated, however, there was a problem that it was difficult to perform each of the plural types of measurements accurately. The description herein discloses a technique that allows plural types of measurements on a subject eye to be performed accurately by using a single ophthalmic apparatus.

A first ophthalmic apparatus disclosed herein may comprise: a first light source configured to output first light to be irradiated to an anterior segment of a subject eye; and a second light source configured to output second light to be irradiated to a retina of the subject eye. The apparatus may be configured capable of executing a first examination using the first light reflected from the anterior segment and a second examination using the second light reflected from the retina. A wavelength of the second light outputted from the second light source may be smaller than a wavelength of the first light outputted from the first light source.

A second ophthalmic apparatus disclosed herein may comprise: a light source configured to output light to be irradiated to a subject eye; a light receiver configured to receive the light of the light source reflected from the subject eye; and a processor. The processor may be configured capable of executing, based on reflected light received by the light receiver: an anterior segment tomographic image acquiring process of acquiring a two-dimensional tomographic image of an anterior segment of the subject eye; a refraction measuring process of measuring refraction of the subject eye; an eye axial length measuring process of measuring an eye axial length of the subject eye; and a retina tomographic image acquiring process of acquiring a two-dimensional tomographic image of a retina of the subject eye.

DETAILED DESCRIPTION

Figure 1:
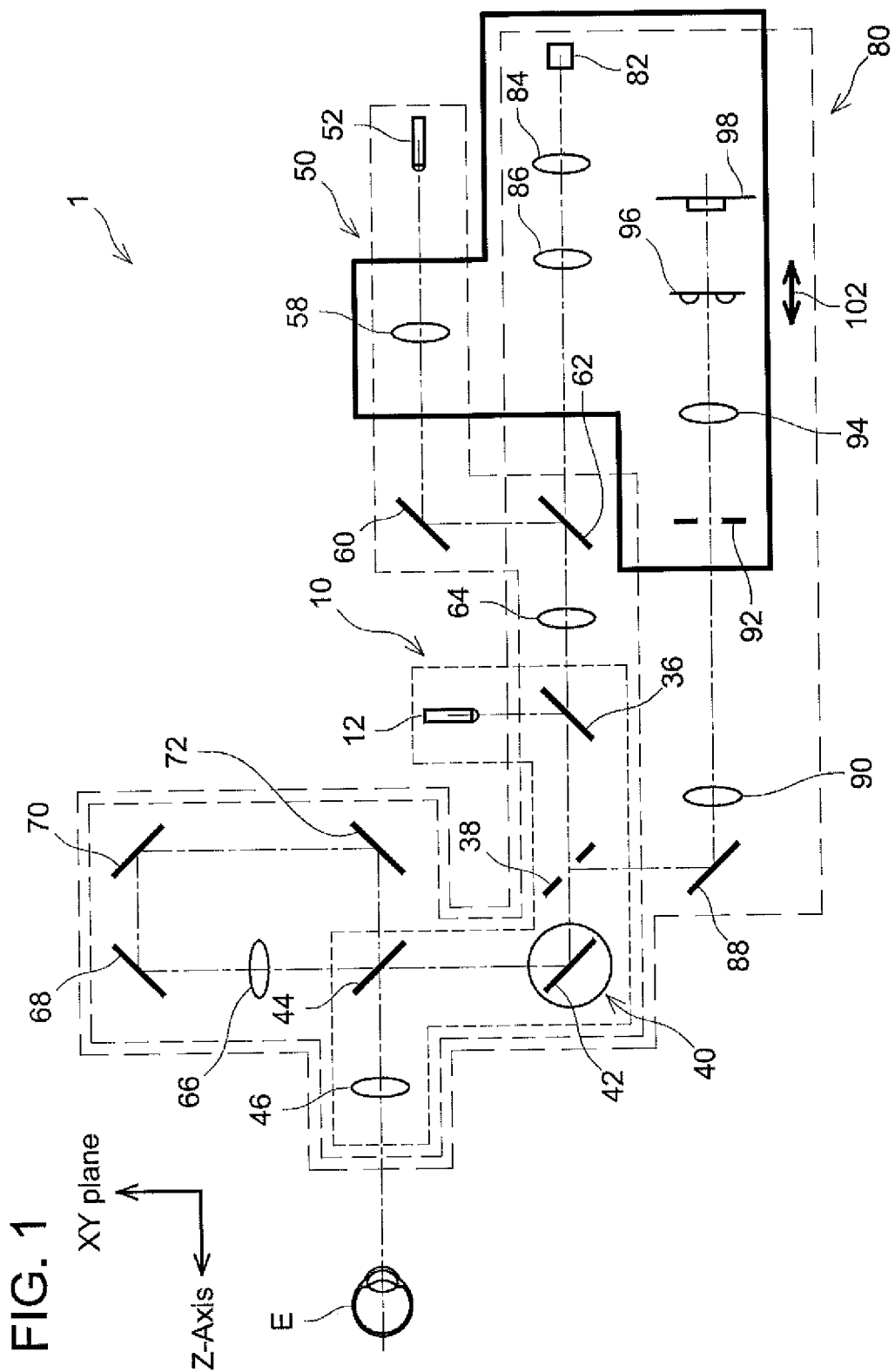
FIG. 1 shows a schematic configuration of an optical system of an ophthalmic apparatus of a first embodiment.

Some of the features characteristic to below-described embodiments will herein be listed. It should be noted that the respective technical elements are independent of one another, and are useful solely or in combinations. The combinations thereof are not limited to those described in the claims as originally filed.

A first ophthalmic apparatus disclosed herein may comprise: a first light source configured to output first light to be irradiated to an anterior segment of a subject eye; and a second light source configured to output second light to be irradiated to a retina of the subject eye. The apparatus may be configured capable of executing a first examination using the first light reflected from the anterior segment and a second examination using the second light reflected from the retina. A wavelength of the second light outputted from the second light source may be smaller than a wavelength of the first light outputted from the first light source.

In the above ophthalmic apparatus, since the wavelength of the second light irradiated to the retina is smaller than the wavelength of the first light irradiated to the anterior segment, the light with suitable wavelengths can be irradiated respectively to the anterior segment and the retina. Due to this, both the first examination executed by irradiating the light to the anterior segment of the subject eye and the second examination executed by irradiating the light to the retina can be performed accurately using a single ophthalmic apparatus.

In the first ophthalmic apparatus disclosed herein, the wavelength of the first light outputted from the first light source may be 0.95 μm or more and 1.80 μm or less. The wavelength of the second light outputted from the second light source may be 0.40 μm or more and 1.15 μm or less. According to this configuration, the light with a more suitable wavelength can be irradiated to each of the anterior segment and the retina. Due to this, the first examination and the second examination can be executed accurately, and an examination result with a greater accuracy can be acquired for the subject eye.

The first ophthalmic apparatus disclosed herein may further comprise a mirror disposed on a first optical path and on a second optical path, the first optical path being an optical path of the first light irradiated from the first light source to the anterior segment of the subject eye and the second optical path being an optical path of the second light irradiated from the second light source to the retina of the subject eye. The mirror may be configured to reflect the first light from the first light source and transmit the second light from the second light source. According to this configuration, an optical path length of the first optical path and an optical path length of the second optical path length can each be adjusted suitably by the light reflection and transmittance on the mirror disposed on the optical paths.

In the first ophthalmic apparatus disclosed herein, the first optical path may include a first optical path section being an optical path of the first light irradiated from the mirror to the subject eye, and the second optical path may include the first optical path section. According to this configuration, the optical path from the mirror to the subject eye is shared between the first and second optical paths. Due to this, the light from two different light sources can be irradiated to the subject eye at different optical path lengths without changing a relative position of the subject eye with respect to the mirror.

In the first ophthalmic apparatus disclosed herein may further comprise a scanner disposed on the first optical path and on the second optical path. The scanner may be configured to scan the first light outputted from the first light source and to scan the second light outputted from the second light source. According to this configuration, the scanner for scanning the first light irradiated to the anterior segment and the scanner for scanning the second light irradiated to the retina can be facilitated by a single scanner. Due to this, a configuration of the ophthalmic apparatus can be suppressed from becoming complicated, and a number of components can be reduced.

In the first ophthalmic apparatus disclosed herein, the scanner may be disposed on the optical path from the first light source to the mirror and on the optical path from the second light source to the mirror. According to this configuration, the mirror and the scanner can suitably be shared between the first and second optical paths by disposing the scanner on a light source side relative to the mirror.

In the first ophthalmic apparatus disclosed herein, the scanner may be configured capable of changing an incident position of the second light outputted from the second light source on the subject eye and an incident angle of the second light relative to the subject eye outputted from the second light source is to be scanned by the scanner, scan may be executed such that progressing directions of light entering the subject eye intersect each other between the retina and a crystalline lens of the subject eye. According to this configuration, the retina of the subject eye can be scanned by the second light by causing the scanner to execute the scan so that the progressing directions of the second light outputted from the second light source intersect each other between the retina and the crystalline lens of the subject eye. Further, for example, even if there is opacity in the crystalline lens of the subject eye, the light outputted from the second light source can be irradiated to the retina while avoiding the opacity in the crystalline lens.

The first ophthalmic apparatus disclosed herein, may further comprise a lens disposed between the mirror and the subject eye. The scanner may be configured capable of changing an incident position of the first light outputted from the first light source on the subject eye, and when the first light outputted from the first light source is to be scanned by the scanner, scan may be executed such that the progressing directions of the light entering the subject eye are parallel to an optical axis of the lens. According to this configuration, the first light can suitably be scanned on the anterior segment of the subject eye by executing the scan so that the progressing directions of the first light outputted from the first light source become parallel to the optical axis of the lens. Further, since the light parallel to the optical axis of the lens enters the subject eye, images with less distortions can be acquired.

The first ophthalmic apparatus disclosed herein, may further comprise a third light source configured to output third light for measuring ocular refraction of the subject eye. A third optical path being an optical path of the third light outputted from the third light source may merge with an optical path section of the second optical path, the optical path section being a section from the second light source to the scanner, and the third light outputted from the third light source may pass through the second optical path and may be irradiated to the retina of the subject eye. According to this configuration, the light from the third light source, which is different from the second light source, can be irradiated to the retina of the subject eye. Due to this, the third examination using the third light reflected from the retina can be executed in addition to the second examination using the second light reflected from the retina. For example, an examination for measuring an ocular refraction of the subject eye may be executed based on the third light, and other examinations may be executed based on the second light. Due to this, each of the second and third examinations can be executed using the light with wavelength that is suitable therefor.

The first ophthalmic apparatus disclosed herein may further comprise a processor configured to calculate a shape of the anterior segment of the subject eye based on reflected light of the first light reflected from the anterior segment of the subject eye and to calculate a shape of the retina of the subject eye and an eye axial length of the subject eye based on reflected light of the second light reflected from the retina of the subject eye. According to this configuration, plural types of measurements on the subject eye are enabled using a single ophthalmic apparatus, and the light with the suitable wavelength can be used for each of the plural types of measurements. Due to this, the plural types of measurements can respectively be executed accurately using the single ophthalmic apparatus.

A second ophthalmic apparatus disclosed herein may comprise: a light source configured to output light to be irradiated to a subject eye; a light receiver configured to receive the light of the light source reflected from the subject eye; and a processor. The processor may be configured capable of executing, based on reflected light received by the light receiver: an anterior segment tomographic image acquiring process of acquiring a two-dimensional tomographic image of an anterior segment of the subject eye; a refraction measuring process of measuring refraction of the subject eye; an eye axial length measuring process of measuring an eye axial length of the subject eye; and a retina tomographic image acquiring process of acquiring a two-dimensional tomographic image of a retina of the subject eye.

In the above ophthalmic apparatus, the two-dimensional tomographic image of the anterior segment, the refraction, the eye axial length, and the two-dimensional tomographic image of the retina can be measured by using the single ophthalmic apparatus. Due to this, diagnosis of disorders of the subject eye and examinations on a visual function thereof can accurately be performed.

The second ophthalmic apparatus disclosed herein may further comprise light concentrating position adjuster configured to adjust a light concentrating position to the retina of the subject eye. The processor may be configured to drive the light concentrating position adjuster based on the refraction of the subject eye measured by the refraction measuring process to adjust the light concentrating position toward the retina of the subject eye, and may be configured to execute at least one of the anterior segment tomographic image acquiring process, the eye axial length measuring process, and the retina tomographic image acquiring process based on reflected light that is obtained by irradiating the light to the subject eye at the adjusted light concentrating position. According to this configuration, at least one of the anterior segment tomographic image acquiring process, the eye axial length measuring process, and the retina tomographic image acquiring process can be executed after having adjusted to a suitable state based on the refraction of the subject eye. Due to this, at least one of the two-dimensional tomographic image of the anterior segment, the eye axial length, and the two-dimensional tomographic image of the retina of the subject eye can be measured more accurately.

The second ophthalmic apparatus disclosed herein may further comprise an irradiation position adjuster configured to adjust an irradiation position of the light outputted from the light source toward the subject eye. The processor may be configured to drive the irradiation position adjuster based on the two-dimensional tomographic image of the anterior segment of the subject eye acquired by the anterior segment tomographic image acquiring process to adjust the irradiation position of the light outputted from the light source toward the subject eye. The processor may be configured to execute at least one of the refraction measuring process, the eye axial length measuring process, and the retina tomographic image acquiring process based on reflected light that is obtained by irradiating the light to the subject eye at the adjusted irradiation position. According to this configuration, at least one of the refraction measuring process, the eye axial length measuring process, and the retina tomographic image acquiring process can be executed after having adjusted the irradiation position of the examination light to the subject eye based on the two-dimensional tomographic image of the anterior segment of the subject eye. Due to this, at least one of the refraction, the eye axial length, and the two-dimensional tomographic image of the retina of the subject eye can be measured more accurately.

In the second ophthalmic apparatus disclosed herein, the processor may be configured to identify a position of an, opaque portion in a crystalline lens based on the two-dimensional tomographic image of the anterior segment of the subject eye acquired by the anterior segment tomographic image acquiring process. The processor may be configured to adjust the irradiation position of the light outputted from the light source toward the subject eye based on the identified position of the opaque portion in the crystalline lens. According to this configuration, the light from the light source can be irradiated to the retina while avoiding the position of the opaque portion of the crystalline lens. Due to this, at least one of the refraction, the eye axial length, and the two-dimensional tomographic image of the retina of the subject eye can be measured more accurately.

First Embodiment

Hereinbelow, an ophthalmic apparatus 1 of a first embodiment will be described. As shown in FIG. 1, the ophthalmic apparatus 1 includes an anterior segment OCT optical system 10 configured to capture tomography of an anterior segment of a subject eye E, and an eye axial length/retinal OCT optical system 50 configured to measure an eye axial length of the subject eye E and capture tomography of a retina of the subject eye E, a reflection measurement optical system 80 configured to measure a refraction of the subject eye E, an alignment optical system (not shown) configured to align the ophthalmic apparatus 1 in a predetermined positional relationship relative to the subject eye E, and an observation optical system (not shown) configured to observe the subject eye E. Since configurations used in conventionally known ophthalmic apparatuses can be used as the alignment optical system and the observation optical system, detailed descriptions therefor will be omitted.

The anterior segment OCT optical system 10 is an optical system used for capturing tomographic images of the anterior segment of the subject eye E by an optical coherence tomography method. In the anterior segment OCT optical system 10, a Fourier domain (optical frequency sweeping) scheme using a wavelength swept light source that executes scan by chronologically changing wavelengths is employed. Shapes of respective portions of the anterior segment of the subject eye E (such as a cornea, an anterior chamber, and a crystalline lens) can be measured from a tomographic image captured by the anterior segment OCT optical system 10. The anterior segment OCT optical system 10 includes an anterior segment OCT interferometer 12, dichroic mirrors 36, 44, a mirror 38 with a circular hole at its center (which may be termed a perforated mirror 38 hereinbelow), a scanner 40, and an object lens 46.

Figure 2:
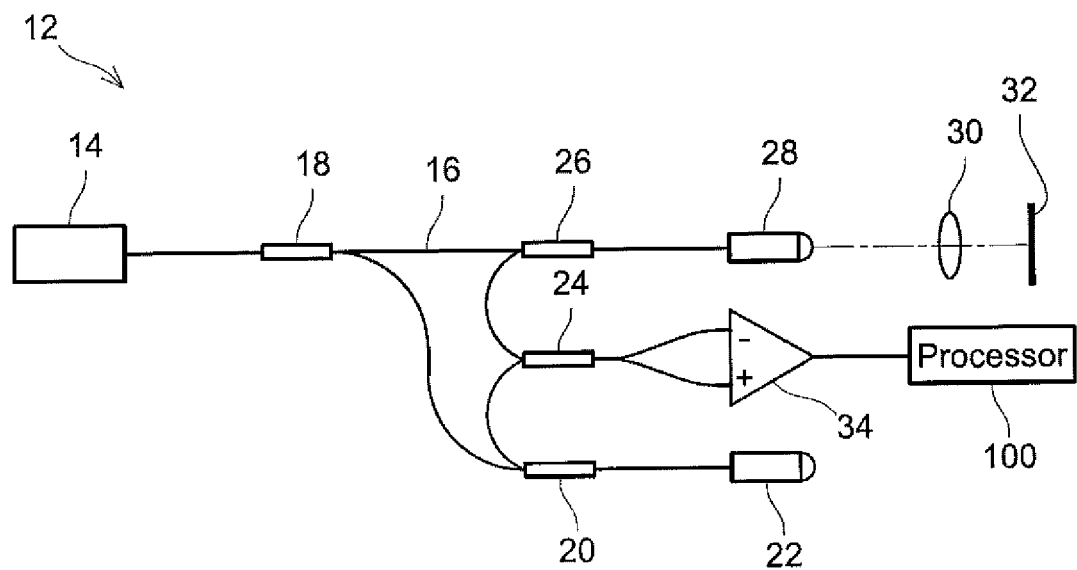
FIG. 2 shows a schematic configuration of an anterior segment OCT interferometer.

The anterior segment OCT interferometer 12 will be described with reference to FIG. 2. As shown in FIG. 2, the anterior segment OCT interferometer 12 includes an anterior segment wavelength swept light source 14, an optical fiber 16, optical couplers 18, 24, light circulators 20, 26, fiber collimators 22, 28, a lens 30, a reference mirror 32, a light receiving element 34, and a zero-point adjustment mechanism (not shown).

Light outputted from the anterior segment wavelength swept light source 14 travels through the optical fiber 16 and is inputted to the optical coupler 18. The light inputted to the optical coupler 18 is split into reference light and measurement light by a ratio of 10:90 in the optical coupler 18, for example, and is outputted therefrom.

The measurement light outputted from the optical coupler 18 travels through the optical fiber 16 and enters the light circulator 20. The measurement light inputted to the light circulator 20 travels through the optical fiber 16 and enters the fiber collimator 22, then is outputted from the fiber collimator 22 (that is, it is outputted from the anterior segment OCT interferometer 12). The measurement light outputted from the anterior segment OCT interferometer 12 travels through optical paths in the anterior segment OCT optical system 10 to be described later, and enters the subject eye E. The measurement light having entered the subject eye E is reflected on the anterior segment of the subject eye E (such as the cornea, the anterior chamber, and the crystalline lens). The reflected light thereof travels through the respective optical paths of the anterior segment OCT optical system 10 in a reverse direction as aforementioned, and enters the fiber collimator 22 again. The reflected light inputted to the fiber collimator 22 travels through the optical fiber 16 and enters the light circulator 20, and from the light circulator 20, it travels through the optical fiber 16 and enters the optical coupler 24.

On the other hand, the reference light outputted from the optical coupler 18 travels through the optical fiber 16 and enters the light circulator 26. The reference light inputted to the light circulator 26 travels through the optical fiber 16 and the fiber collimator 28, and enters the reference mirror 32 through the lens 30. An optical path length of the reference light outputted from the anterior segment wavelength swept light source 14 is adjusted by the zero-point adjustment mechanism (not shown). Since a configuration used in the conventionally known ophthalmic apparatuses can be used as the zero-point adjustment mechanism, the detailed description thereof will be omitted. The reference light reflected on the reference mirror 32 travels through the fiber collimator 28 again and enters the optical fiber 16, then travels through the optical fiber 16 and enters the light circulator 26. Further, the reference light inputted to the light circulator 26 travels through the optical fiber 16 and enters the optical coupler 24.

In the optical coupler 24, the reflected light from the subject eye E and the reference light are multiplexed, and a signal thereof travels through the optical fiber 16 and is inputted to the light receiving element 34. As the light receiving element 34, for example, an indium-gallium-arsenic (InGaAs)-based light receiving element can be used, and coherence for each wavelength is measured in the light receiving element 34. The measured coherence signal is inputted to a processor 100. In the processor 100, processes such as Fourier transform is performed on the coherence signal, and a tomographic image of the anterior segment along a scan line is thereby acquired.

The anterior segment wavelength swept light source 14 outputs light with a long wavelength, and in this embodiment, it outputs light with a center wavelength of 1.31 µm. The anterior segment wavelength swept light source 14 may output light with the center wavelength of 0.95 µm or more and 1.80 µm or less. When the light with the long wavelength is used, for example, it becomes easier for the light to pass through opacity of the crystalline lens and strong-scattering tissues such as ciliary, conjunctiva, and sclera, and further, due to its large absorbance by water, the light is less likely to reach the retina, which allows stronger light to be irradiated. Due to this, by outputting the light with the center wavelength of 0.95 µm or more from the anterior segment wavelength swept light source 14, reach to tissues constituted of scattering substances can be increased. Further, the light with the wavelength of 0.95 µm or more and 1.15 µm or less does not scatter so much by water, and as such, irradiation of the light in this range to the subject eye E allows an anterior segment OCT image with a good image quality to be acquired. Further, by outputting the light with the center wavelength of 1.80 µm or less from the anterior segment wavelength swept light source 14, measurement can be executed using the indium-gallium-arsenic (InGaAs)-based light receiving element with high sensitivity. As such, with the light with the center wavelength of 0.95 µm or more and 1.80 µm or less being outputted from the anterior segment wavelength swept light source 14, the light with the suitable wavelength for capturing tomographic images of the anterior segment of the subject eye E can be outputted. The anterior segment wavelength swept light source 14 is an example of a "first light source".

The light outputted from the anterior segment wavelength swept light source 14 is emitted from the anterior segment OCT interferometer 12 and is irradiated to the dichroic mirror 36. The dichroic mirror 36 reflects light with the wavelength of 1.20 µm or more and transmits light with the wavelength less than 1.20 µm. As aforementioned, the light emitted from the anterior segment OCT interferometer 12 is light having the center wavelength of 1.31 µm, so it is reflected on the dichroic mirror 36. The light reflected from the dichroic mirror 36 travels through the circular hole at a center of the perforated mirror 38, and is irradiated to the scanner 40. The scanner 40 is for example a galvanometer, and an irradiating direction of the light is changed to a predetermined direction by a Galvano mirror 42 attached to the galvanometer. The light emitted from the scanner 40 is irradiated to the dichroic mirror 44. The dichroic mirror 44 reflects light with the wavelength of 1.20 µm or more and transmits light with the wavelength less than 1.20 µm. The light emitted from the scanner 40 is light having the center wavelength of 1.31 µm, so it is reflected on the dichroic mirror 44. Then, the light reflected from the dichroic mirror 44 is irradiated to the anterior segment of the subject eye E through the object lens 46. Reflected light from the anterior segment of the subject eye E enters the anterior segment OCT interferometer 12 through the object lens 46, the dichroic mirror 44, the scanner 40, the perforated mirror 38, and the dichroic mirror 36. As aforementioned, when the reflected light from the subject eye E enters the anterior segment OCT interferometer 12, it is multiplexed with the reference light and the coherence for each wavelength is measured in the light receiving element 34. The measured coherence signal is inputted to the processor 100.

Figure 3:
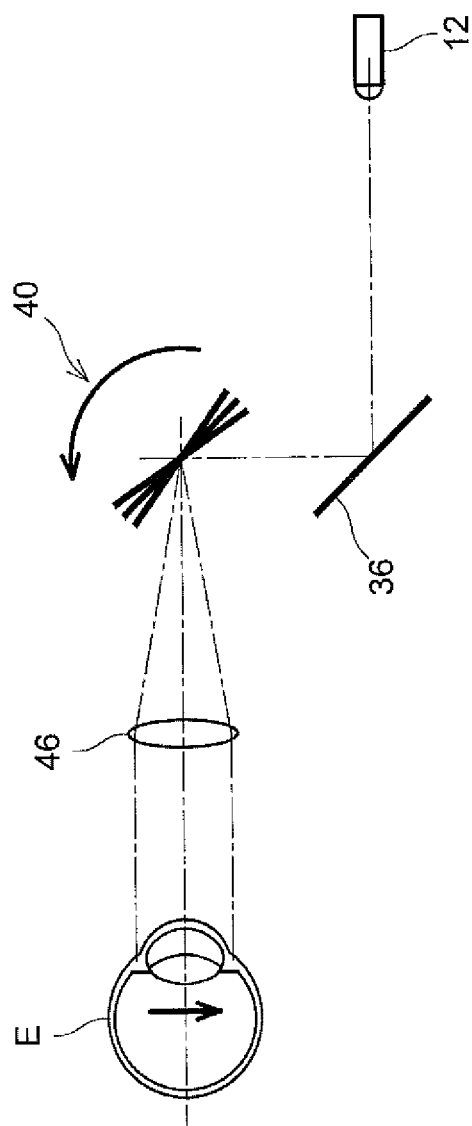
FIG. 3 schematically shows an optical path through which light outputted from the anterior segment OCT interferometer is irradiated to a subject eye.

Scan in the anterior segment OCT optical system 10 will be described with reference to FIG. 3. FIG. 3 shows the optical path through which the light outputted from the anterior segment OCT interferometer 12 is irradiated to the subject eye E, and only some of optical members disposed on the optical path (that is, the dichroic mirror 36, the scanner 40, and the object lens 46) are shown, and other optical members are omitted from the drawing. As shown in FIG. 3, in the anterior segment OCT optical system 10, the scanner 40 is disposed at a posterior focal point of the object lens 46. Due to this, the light scanned by the scanner 40 is irradiated parallel to an optical axis with respect to the subject eye E. That is, telecentric scan is executed in the anterior segment OCT optical system 10, and an image without distortion can be acquired in tomographic image capture of the subject eye E. Further, in the anterior segment OCT interferometer 12, an end surface of the optical fiber 16 from which the light is emitted is disposed at a position conjugate with the anterior segment of the subject eye E. Due to this, the light emitted from the anterior segment OCT interferometer 12 can be concentrated to the anterior segment of the subject eye E. Thus, the anterior segment OCT optical system 10 can suitably capture tomography of the anterior segment of the subject eye E.

The eye axial length/retinal OCT optical system 50 is an optical system used to capture the retina of the subject eye E by the optical coherence tomography method. Shapes of respective portions of the retina of the subject eye E (such as retina and choroid) can be measured and the eye axial length of the subject eye E can be measured from the tomographic image captured by the eye axial length/retinal OCT optical system 50. Further, by using the eye axial length/retinal OCT optical system 50, the ophthalmic apparatus 1 can be used as an SLO (Scanning Laser Ophthalmoscope) for observing the retina of the subject eye E. The eye axial length/retinal OCT optical system 50 includes an eye axial length and retinal OCT interferometer 52, lenses 58, 64, 66, mirrors 60, 68, 70, 72, dichroic mirrors 36, 44, 62, the perforated mirror 38, the scanner 40, and the object lens 46. The eye axial length and retinal OCT interferometer 52 differs from the aforementioned anterior segment OCT interferometer 12 in that it includes a retina wavelength swept light source 54 and a light receiving element 56 (see FIG. 5) instead of the anterior segment wavelength swept light source 14 and the light receiving element 34, and other configurations thereof are substantially identical to those of the anterior segment OCT interferometer 12. Due to this, detailed descriptions of the configurations identical to those of the anterior segment OCT interferometer 12 will be omitted. As the light receiving element 56, for example, a silicon-based light receiving element may be used.

The retina wavelength swept light source 54 outputs light with a wavelength different from that of the light outputted from the anterior segment wavelength swept light source 14, and in this embodiment, it outputs light with a center wavelength of 1.06 μm. The retina wavelength swept light source 54 may output light with the center wavelength of 0.40 μm or more and 1.15 μm or less. The light with the center wavelength of 0.40 μm or more and 1.15 μm or less has a high intraocular transmittance. Due to this, by outputting the light with the center wavelength of 0.40 μm or more and 1.15 μm or less from the retina wavelength swept light source 54, the light outputted from the retina wavelength swept light source 54 can sufficiently be irradiated to the retina of the subject eye E. Further, the silicon-based light receiving element (or camera) has high sensitivity to the light with the wavelength of 0.40 μm or more and 0.95 μm or less. Further, since the light with the wavelength of 0.95 μm or more and 1.15 μm or less does not scatter so much by water, and as such, the irradiation of the light in this range to the subject eye E allows an OCT image with a good image quality to be acquired. The light with the center wavelength of 0.40 μm or more and 1.15 μm or less being outputted from the retina wavelength swept light source 54, the light with the suitable wavelength for capturing images of the retina of the subject eye E can be outputted. The retina wavelength swept light source 54 is an example of a "second light source".

The light outputted from the retina wavelength swept light source 54 is outputted from the eye axial length and retinal OCT interferometer 52, and is irradiated to the mirror 60 through the lens 58. A position of the lens 58 can be moved along the optical axis by a focal point adjusting mechanism 102 to be described later. The light emitted to the mirror 60 is irradiated to the dichroic mirror 62. The dichroic mirror 62 reflects light with the wavelength of 0.90 μm or more and transmits light with the wavelength less than 0.90 μm. As aforementioned, the light irradiated to the mirror 60 is light with the center wavelength of 1.06 μm, so it is reflected on the dichroic mirror 62. The light reflected on the dichroic mirror 62 is irradiated to the dichroic mirror 36 through the lens 64. As aforementioned, since the dichroic mirror 36 transmits the light with the wavelength less than 1.20 μm, the light that passed through the lens 64, which is the light with the center wavelength of 1.06 μm, passes through the dichroic mirror 36. Here, an optical path of the eye axial length/retinal OCT optical system 50 comes to be a same optical path as the anterior segment OCT optical system 10.

The light passed through the dichroic mirror 36 passes through the circular hole at the center of the perforated mirror 38, and is irradiated to the scanner 40. The light irradiated to the scanner 40 has the irradiating direction of the light changed to a predetermined direction, and is irradiated to the dichroic mirror 44. As aforementioned, since the dichroic mirror 44 transmits the light with the wavelength less than 1.20 μm, the light irradiated to the scanner 40, which is the light with the center wavelength of 1.06 μm, passes through the dichroic mirror 44.

As aforementioned, in the anterior segment OCT optical system 10, since the light irradiated to the scanner 40 is the light with the center wavelength of 1.31 μm, it is reflected on the dichroic mirror 44. Due to this, the optical path of the eye axial length/retinal OCT optical system 50 comes to be a same optical path as the anterior segment OCT optical system 10 from the dichroic mirror 36 to the dichroic mirror 44 via the perforated mirror 38 and the scanner 40, and for its portion from the dichroic mirror 44, the optical path becomes a different optical path from the anterior segment OCT optical system 10.

The light that passed through the dichroic mirror 44 passes through the lens 66, and is reflected on the mirrors 68, 70, 72. The light reflected on the mirror 72 is irradiated again to the dichroic mirror 44, and as aforementioned, it passes through the dichroic mirror 44. Here, the optical path of the eye axial length/retinal OCT optical system 50 again becomes same as that of the anterior segment OCT optical system 10.

The light that passed through the dichroic mirror 44 is irradiated to the subject eye E through the object lens 46. That is, the optical path of the eye axial length/retinal OCT optical system 50 comes to be the same optical path as the anterior segment OCT optical system 10 from the dichroic mirror 44 to the subject eye E via the object lens 46. Thus, the optical path of the eye axial length/retinal OCT optical system 50 becomes the same optical path as the anterior segment OCT optical system 10 from the dichroic mirror 36 to the dichroic mirror 44 via the scanner 40, becomes a different optical path from the anterior segment OCT optical system 10 from the dichroic mirror 44 and back to its way of being irradiated to the dichroic mirror 44 again via the lens 66, and then becomes the same optical path as the anterior segment OCT optical system 10 from the dichroic mirror 44 to the subject eye E via the object lens 46.

The reflected light from the subject eye E is inputted to the eye axial length and retinal OCT interferometer 52 through the object lens 46, the dichroic mirror 44, the mirrors 72, 70, 68, the lens 66, the dichroic mirror 44, the scanner 40, the perforated mirror 38, the dichroic mirror 36, the lens 64, the dichroic mirror 62, the mirror 60, and the lens 58. Similar to the anterior segment OCT interferometer 12 as aforementioned, when the reflected light from the subject eye E enters the eye axial length and retinal OCT interferometer 52, it is multiplexed with the reference light, and the coherence for each wavelength is measured in the light receiving element 56. Then, the measured coherence signal is inputted to the processor 100.

Figure 4:
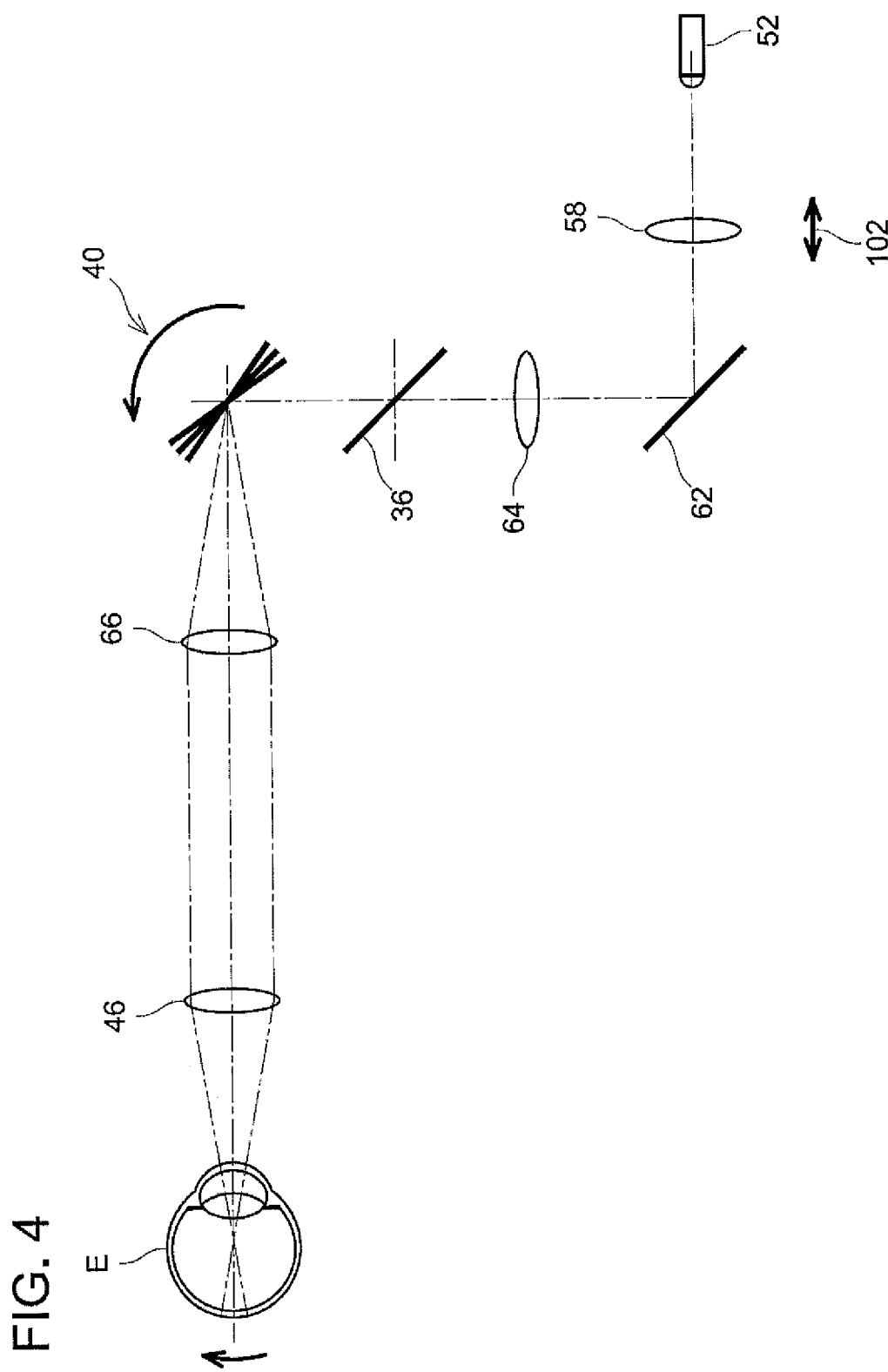
FIG. 4 schematically shows an optical path through which light outputted from an eye axial length/retinal OCT interferometer is irradiated to the subject eye.

Scan in the eye axial length/retinal OCT optical system 50 will be described with reference to FIG. 4. FIG. 4 shows the optical path through which the light outputted from the eye axial length and retinal OCT interferometer 52 is irradiated to the subject eye E, and only some of optical members disposed on the optical path (that is, the lenses 58, 64, 66, the dichroic mirrors 36, 62, the scanner 40, and the object lens 46) are shown, and other optical members are omitted from the drawing. As shown in FIG. 4, in the eye axial length/retinal OCT optical system 50, two lenses 46, 66 are disposed between the scanner 40 and the subject eye E. Further, the scanner 40 is disposed at a position conjugate with an intraocular part of the subject eye E. Due to this, pivot scan forming a pivot intraocularly in the subject eye E is executed in the eye axial length/retinal OCT optical system 50. In general, with the case of the pivot scan, the pivot is formed in a pupil of the subject eye E, so it becomes difficult to sufficiently irradiate the light to the retina when for example an opaque portion exists in the crystalline lens of the subject eye E. In this embodiment, since the pivot is formed between the retina and the crystalline lens of the subject eye E, the light can easily be irradiated to the retina regardless of a state of the crystalline lens of the subject eye E.

Further, in the eye axial length and retinal OCT interferometer 52, an end surface of the optical fiber 16 from which the light is emitted is disposed at a position conjugate with the retina of the subject eye E. Due to this, the light emitted from the eye axial length and retinal OCT interferometer 52 can be concentrated at the retina of the subject eye E. The position of the lens 58 can be changed by actuating the focal point adjusting mechanism 102 to be described later. Due to this, the light emitted from the eye axial length and retinal OCT interferometer 52 can be concentrated at the retina of the subject eye E according to the refraction of the subject eye E. Thus, the tomography of the retina of the subject eye E can suitably be captured by the eye axial length/retinal OCT optical system 50.

The ophthalmic apparatus 1 of the present embodiment executes both the scan in the anterior segment OCT optical system 10 and the scan in the eye axial length/retinal OCT optical system 50 by the scanner 40. Due to this, the configuration in the ophthalmic apparatus 1 is suppressed from becoming complicated, and a number of components can be reduced.

The reflection measurement optical system 80 is an optical system used for measuring the refraction of the subject eye E. The reflection measurement optical system 80 includes a reflection measurement light source 82, lenses 64, 66, 84, 86, 90, 94, the dichroic mirrors 36, 44, 62, the perforated mirror 38, the scanner 40, mirrors 68, 70, 72, 88, the object lens 46, an aperture 92, a ring lens 96, a sensor 98, the focal point adjusting mechanism 102, and a fogging mechanism (not shown).

The reflection measurement light source 82 outputs light with a wavelength different from each wavelength of the light outputted from the anterior segment wavelength swept light source 14 and the light outputted from the retina wavelength swept light source 54, and in this embodiment, it outputs light with a center wavelength of 0.88 nm. The reflection measurement light source 82 may output light with the wavelength of 0.70 µm or more and 0.95 µm or less. The light with the wavelength of 0.70 µm or more and 0.95 µm or less has a high intraocular transmittance. Further, the light with the wavelength of 0.70 µm or more and 0.95 µm or less has a low spectral luminous efficiency to the subject eye E, and is suitable for visual function evaluation since a subject does not so much feel brightness while the light is close to visible light. Due to this, by outputting the light with the wavelength of 0.70 µm or more and 0.95 µm or less from the reflection measurement light source 82, the light from the light source can sufficiently be irradiated to the retina of the subject eye E, and the light with the suitable wavelength for measuring the refraction of the subject eye E can be outputted. The reflection measurement light source 82 is an example of a "third light source".

The light outputted from the reflection measurement light source 82 is irradiated to the dichroic mirror 62 through the lenses 84, 86. As aforementioned, since the dichroic mirror 62 transmits the light with the wavelength less than 0.90 µm, the light that passes through the light lens 86, being light with the center wavelength of 0.88 µm, passes through the dichroic mirror 62. Here, an optical path of the reflection measurement optical system 80 becomes the same as the optical path of the eye axial length/retinal OCT optical system 50. In the eye axial length/retinal OCT optical system 50, aside from the dichroic mirror 62, there are two other dichroic mirrors 36, 44 disposed on the optical path from the dichroic mirror 62 to the subject eye E. Since both of the two dichroic mirrors 36, 44 transmit the light with the wavelength less than 1.20 µm, both the light with the center wavelength of 1.06 µm outputted from the retina wavelength swept light source 54 and light with the center wavelength of 0.88 µm outputted from the reflection measurement light source 82 pass through the dichroic mirrors 36, 44. Due to this, in the reflection measurement optical system 80, the light that passed through the dichroic mirror 62 travels through the same optical path as that of the eye axial length/retinal OCT optical system 50 until it is irradiated to the subject eye E. That is, the optical path of the reflection measurement optical system 80 becomes the same as the optical path of the eye axial length/retinal OCT optical system 50 from the dichroic mirror 62 to the subject eye E. Accordingly, in the reflection measurement optical system 80, the light that passes through the dichroic mirror 62 is irradiated to the subject eye E through the lens 64, the dichroic mirror 36, the perforated mirror 38, the scanner 40, the dichroic mirror 44, the lens 66, the mirrors 68, 70, 72, the dichroic mirror 44, and the object lens 46.

Reflected light from the subject eye E is irradiated to the perforated mirror 38 through the object lens 46, the dichroic mirror 44, the mirrors 72, 70, 68, the lens 66, the dichroic mirror 44, and the scanner 40. The light irradiated to the perforated mirror 38 is reflected on a reflection surface disposed in a periphery of the circular hole provided in the perforated mirror 38, and is further reflected on the mirror 88. The light reflected on the mirror 88 is detected by the sensor 98 through the lens 90, the aperture 92, the lens 94, and the ring lens 96. The ring lens 96 includes a ring-shaped lens portion disposed on a lens 94 side and a light shielding portion disposed on a sensor 98 side. The light shielding portion has light shielded at its portion other than a portion connecting to the lens portion. When light is irradiated to the ring lens 96, ring-shaped light is irradiated from the ring lens 96. The sensor 98 detects the ring-shaped light irradiated from the ring lens 96. The sensor 98 is for example a CCD camera, and an image detected (captured) by the sensor 98 is inputted to the processor 100.

The reflection measurement optical system 80 has an optical path that is same as that of the eye axial length/retinal OCT optical system 50 from the scanner 40 to the subject eye E. Due to this, it executes the pivot scan, similar to the eye axial length/retinal OCT optical system 50. Due to this, similar to the eye axial length/retinal OCT optical system 50, the reflection measurement optical system 80 can irradiate light to the retina regardless of the state of the crystalline lens of the subject eye E. Further, by scanning on the retina, a satisfactory image can be acquired even in cases where factors, such as retinal disorders or blood vessels, that attenuate the reflection from the retina exist.

Further, the reflection measurement optical system 80 includes the focal point adjusting mechanism 102. The focal point adjusting mechanism 102 includes an actuating device (not shown) that integrally moves the reflection measurement light source 82, the lenses 84, 86, 94, the aperture 92, the ring lens 96, and the sensor 98, as well as the lens 58 of the eye axial length/retinal OCT optical system 50 in an optical axis direction (Z-axis direction). The focal point adjusting mechanism 102 can integrally move a position of the reflection measurement light source 82 and a position of the sensor 98 by actuating the actuating device. Due to this, the position of the reflection measurement light source 82 and the position of the sensor 98 can be moved to the positions conjugate with the position of the subject eye E according to the refraction of the subject eye E, and reflection measurement can be executed with high accuracy. The focal point adjusting mechanism 102 is an example of a "light concentrating position adjuster".

Figure 5:
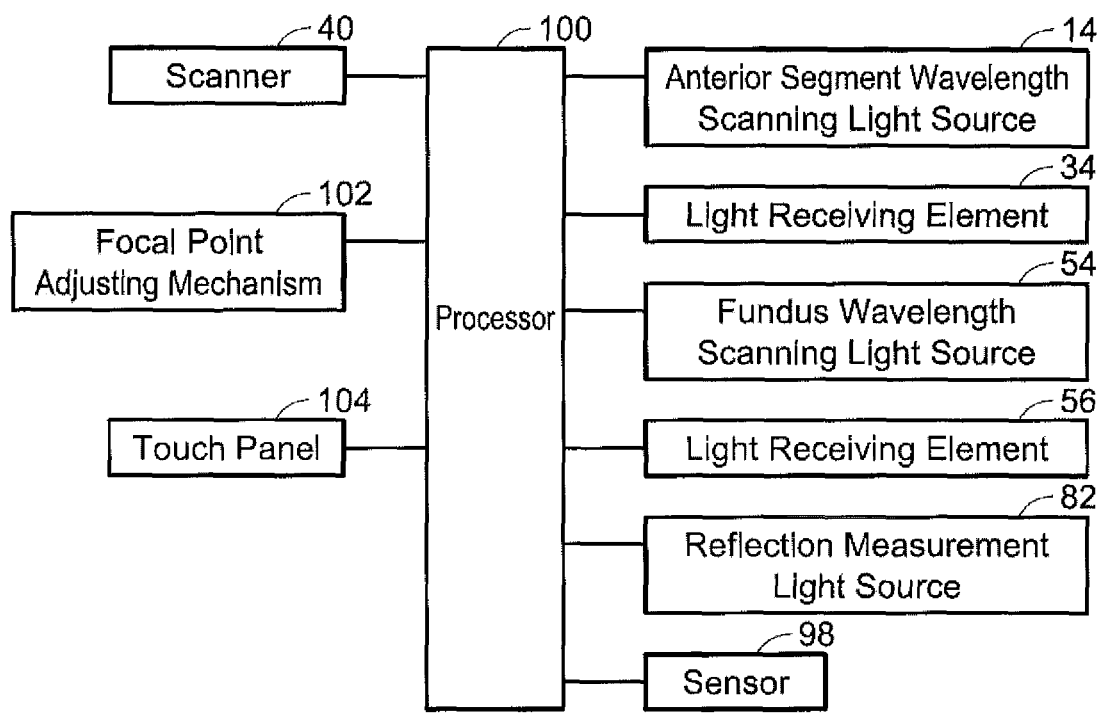
FIG. 5 is a block diagram showing a control system of the ophthalmic apparatus of the first embodiment.

A configuration of a control system of the ophthalmic apparatus 1 of the present embodiment will be described with reference to FIG. 5. As shown in FIG. 5, the ophthalmic apparatus 1 is controlled by the processor 100. The processor 100 is constituted of a microcomputer (microprocessor) constituted of a CPU, a ROM, a RAM, and the like. The processor 100 is connected to the anterior segment wavelength swept light source 14 and the light receiving element 34 in the anterior segment OCT interferometer 12, the retina wavelength swept light source 54 and the light receiving element 56 in the eye axial length and retinal OCT interferometer 52, the reflection measurement light source 82, the sensor 98, the scanner 40, the focal point adjusting mechanism 102, and a touch panel 104.

The processor 100 controls on and off of the anterior segment wavelength swept light source 14 and drives the scanner 40 to scan the light irradiated to the anterior segment of the subject eye E. Further, the coherence signal which corresponds to an intensity of coherence light detected in the light receiving element 34 is inputted to the processor 100. The processor 100 calculates the shapes of the respective tissues in the anterior segment by identifying the positions of the respective parts of the anterior segment of the subject eye E (such as the cornea, the anterior chamber, and the crystalline lens) by subjecting the coherence signal from the light receiving element 34 to Fourier transform. Similarly, the processor 100 controls on and off of the retina wavelength swept light source 54 and drives the scanner 40 to scan the light irradiated to the retina of the subject eye E. Further, the coherence signal which corresponds to an intensity of coherence light detected in the light receiving element 56 is inputted to the processor 100. The processor 100 calculates the shape of the retina and the eye axial length of the subject eye E by identifying the positions of the respective parts of the subject eye E (such as the anterior segment including the cornea and the like, the retina, and the choroid) by subjecting the coherence signal from the light receiving element 56 to Fourier transform. Further, the processor 100 controls on and off of the reflection measurement light source 82 and drives the scanner 40 to scan the light irradiated to the subject eye E. Further, an electric signal detected by the sensor 98 (image captured thereby) is inputted to the processor 100, and the processor 100 calculates the refraction of the subject eye E based on the inputted image. Inputted data and calculation results in the processor 100 are stored in a memory (not shown).

Further, the processor 100 controls the touch panel 104. The touch panel 104 is a display device for providing various types of information related to the measurement results of the subject eye E to an examiner, and also accepts instructions and information from the examiner. For example, the touch panel 104 can display the tomographic images of the anterior segment and the retina of the subject eye E generated in the processor 100, the refraction thereof calculated in the processor 100, and data acquired by the scans. Further, various settings of the ophthalmic apparatus 1 can be inputted on the touch panel 104. The ophthalmic apparatus 1 of the present embodiment is provided with the touch panel 104, however, no limitation is made to this configuration. Any configuration capable of displaying and inputting the aforementioned information may be employed, and a monitor and an input device (such as a mouse and a keyboard) may be provided.

Figure 6:
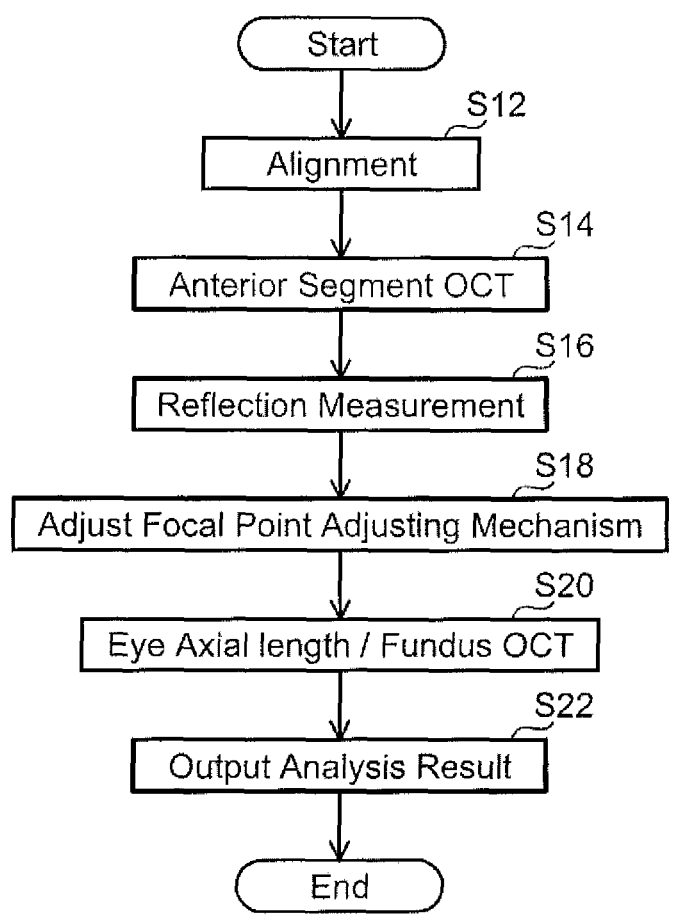
FIG. 6 is a flow chart showing an example of a process to execute plural types of measurements on the subject eye using the ophthalmic apparatus of the first embodiment.
Figure 7:
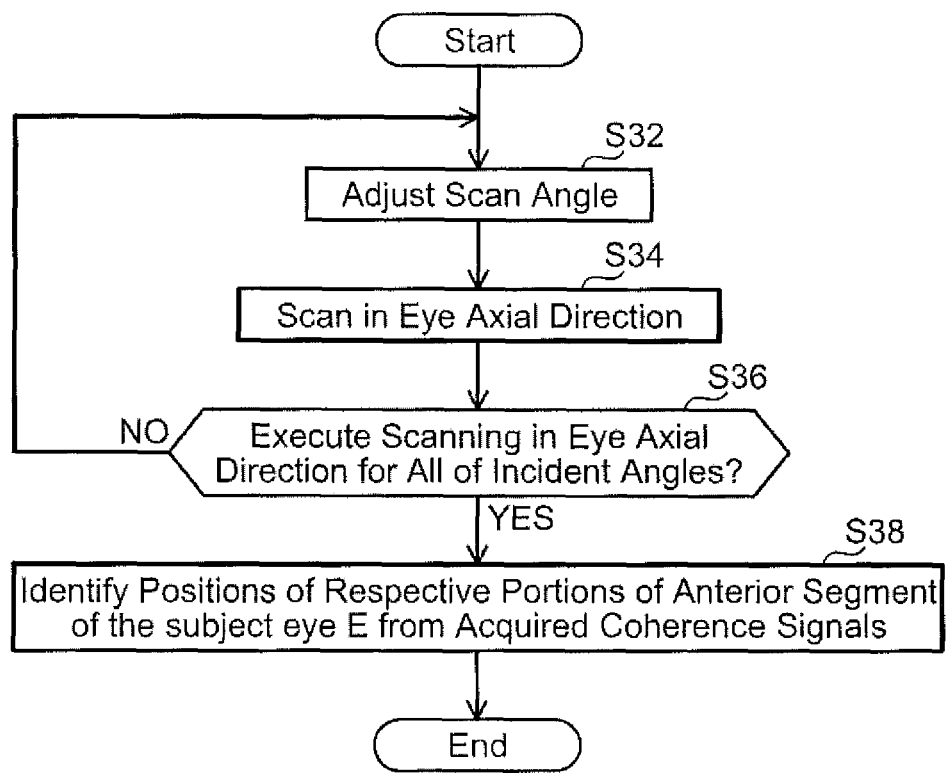
FIG. 7 is a flow chart showing an example of a process of an anterior segment OCT measurement.

With reference to FIGS. 6 to 13, processes of measuring the anterior segment, the retina, the eye axial length, and the refraction of the subject eye E using the ophthalmic apparatus 1 will be described. FIG. 6 is a flow chart showing an example of the process of executing plural types of measurements on the subject eye E using the ophthalmic apparatus 1. As shown in FIG. 6, firstly, when the examiner inputs an instruction to start an examination on the touch panel 104, the processor 100 executes alignment of the subject eye E and the ophthalmic apparatus 1 (S12). The alignment is executed using the alignment optical system (not shown) provided in the ophthalmic apparatus 1. Since methods used in well-known ophthalmic apparatuses can be used for the alignment using the alignment optical system, detailed description thereof will be omitted.

When the alignment is completed, tomographic image capture of the anterior segment of the subject eye E (anterior segment OCT measurement) is executed (S14). Here, the anterior segment OCT measurement in step S14 will be described with reference to FIG. 7. Firstly, as shown in FIG.

7, the processor 100 adjusts the Galvano mirror 42 to a scan angle within a scan angle range (S32). By so doing, the light from the anterior segment wavelength swept light source 14 enters the subject eye E at an incident position and an incident angle corresponding to the adjusted scan angle.

Figure 8A:
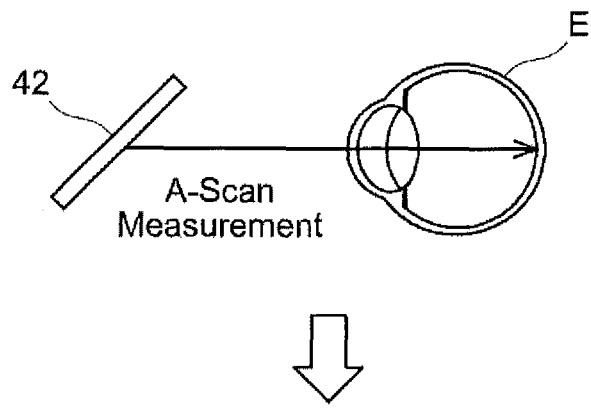
FIGS. 8A to C are diagrams for explaining a procedure for processing a coherence signal waveform obtained by scanning a wavelength of an anterior segment wavelength swept light source of an anterior segment OCT optical system.
Figure 8B:
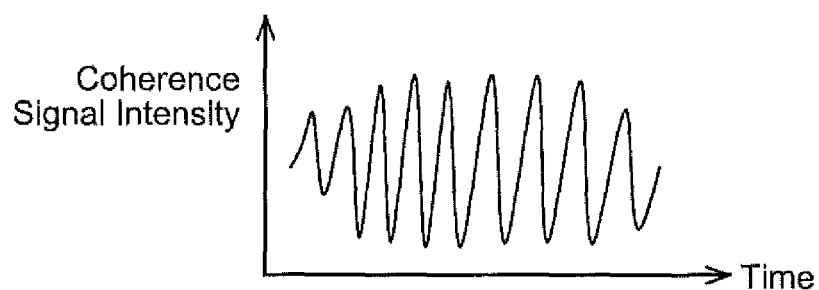
Figure 8C:
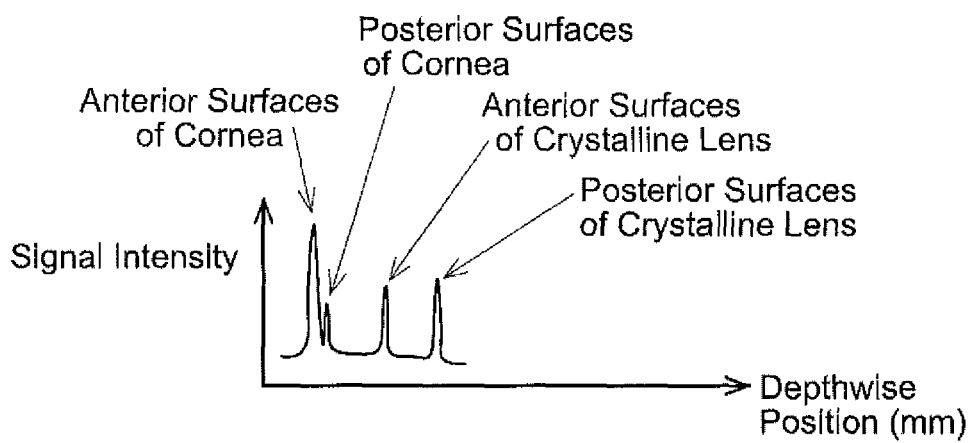

When the adjustment of the Galvano mirror 42 is completed, the processor 100 turns on the anterior segment wavelength swept light source 14 and collects the coherence signal detected by the light receiving element 34 while changing a frequency of the light irradiated from the anterior segment wavelength swept light source 14 (S34). The coherence signal outputted from the light receiving element 34 is a signal of which signal intensity changes chronologically as shown in FIGS. 8A to C, and this signal becomes a signal based on interference waves obtained by multiplexing the reflected light reflected from the respective portions of the subject eye E (such as anterior and posterior surfaces of the cornea and anterior and posterior surfaces of the crystalline lens) and the reference light. As such, the processor 100 separates coherence signal components of the reflected light reflected from the respective portions of the subject eye E (such as the anterior and posterior surfaces of the cornea and the anterior and posterior surfaces of the crystalline lens) from this signal by subjecting the signal inputted from the light receiving element 34 to Fourier transform. Due to this, the processor 100 can identify the depthwise positions of the respective portions of the subject eye E. Acquisition of the coherence signal including the depthwise positional information of the respective portions of the subject eye E by changing the frequency of the light irradiated from the light source will herein be termed an A-scan.

Next, the processor 100 determines whether or not the measurement of step S34 has been executed for all of scan angles that were set in advance prior to the measurement (that is, for all of the incident positions and the incident angles) (S36). In a case where the measurement of step S34 has not been executed for all the scan angles (NO in step S36), the processor 100 returns to step S32, and the processes from step S32 are repeated. Due to this, the coherence signal obtained by the A-scan for each scan angle for scanning the Galvano mirror 42 is thereby acquired. Causing the position where the light from the light source enters and the incident angle thereof to change by changing the scan angle of the Galvano mirror 42 will herein be termed a B-scan.

Figure 9A:
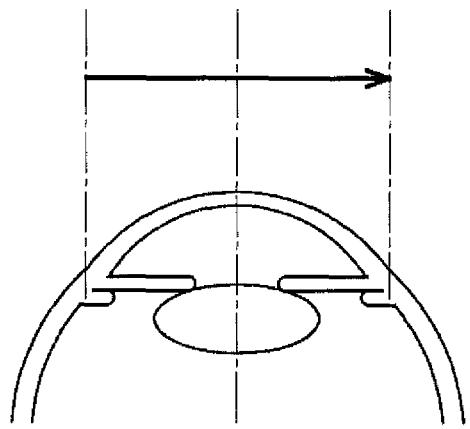
FIGS. 9A, B are diagrams for explaining a procedure for identifying a position of each portion of the subject eye from information acquired for each incident position (information acquired from the procedure shown in FIGS. 8A to C) by scanning the incident positions of light to the subject eye within a predetermined range.
Figure 9B:
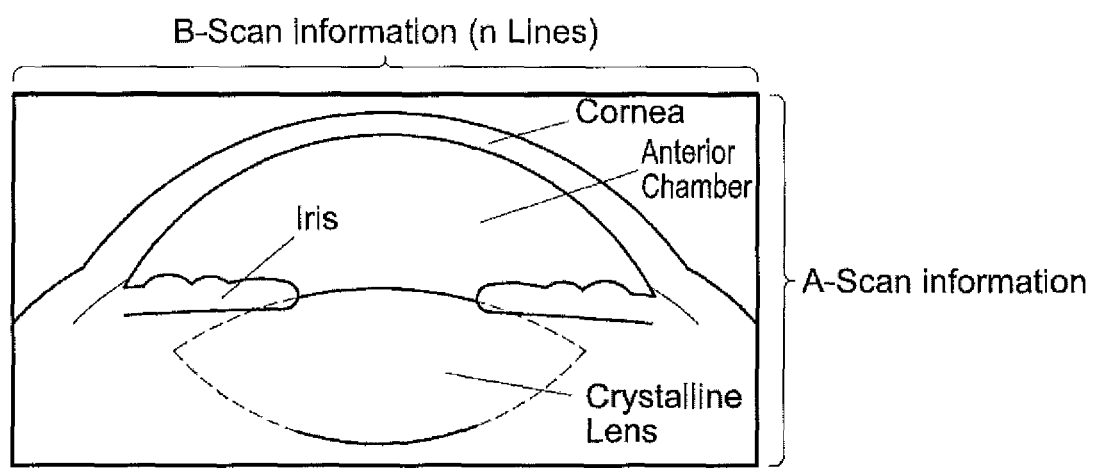

In a case where the measurement of step S34 has been executed for all the scan angles (YES in step S36), the processor 100 identifies the positions of the respective portions of the subject eye E (such as the anterior and posterior surfaces of the cornea and the anterior and posterior surfaces of the crystalline lens) from the coherence signals acquired for the respective scan angles (S38). Specifically, when the process of step S34 is executed for the respective scan angles, information on the coherence signals (A-scan information) is acquired for those scan angles. Accordingly, as shown in FIGS. 9A, B, two-dimensional information in which the coherence signal information (A-scan information) is arranged by a number of the scan angles (n lines) is acquired. Due to this, the processor 100 identifies the positions of the respective portions of the subject eye E by calculating borderlines between the respective portions of the subject eye E (such as the cornea, the anterior chamber, an iris, and the crystalline lens) included in the respective coherence signal information.

Figure 10A:
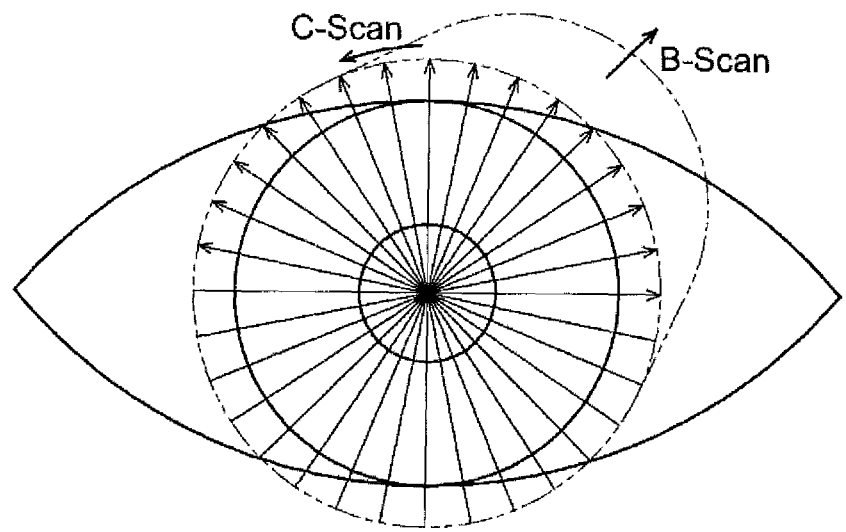
FIGS. 10A, B are diagrams for explaining a radial scanning scheme in the anterior segment OCT measurement.
Figure 10B:
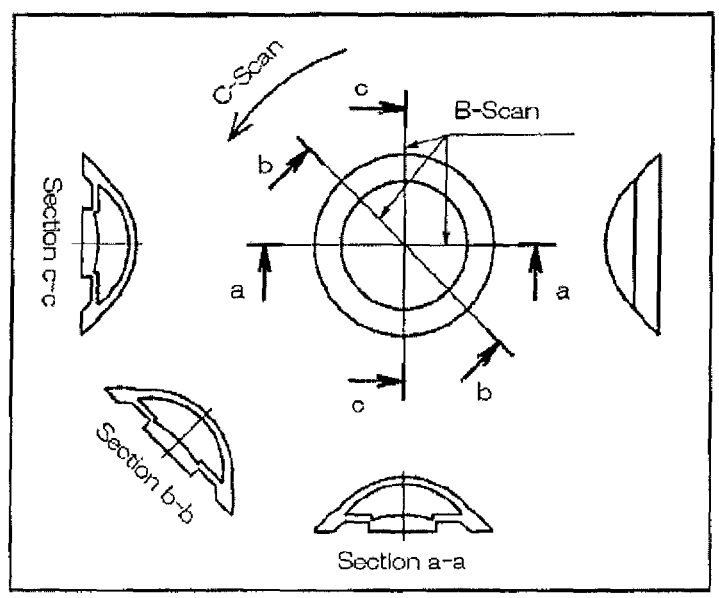

In this embodiment, the anterior segment OCT measurement in step S14 is executed by a radial scan scheme shown in FIGS. 10A, B. Due to this, the tomographic image of the anterior segment is obtained over an entire region. That is, a B-scan direction is set in a radial direction from an apex of the cornea of the subject eye E, and the tomographic image acquisition is executed with a C-scan direction set to a circumferential direction. The processor 100 writes acquired (captured) tomographic image data in the memory.

As aforementioned, the anterior segment OCT optical system 10 executes the telecentric scan. Due to this, a tomographic image without distortion can be acquired in the anterior segment OCT in step S14. Further, the anterior segment OCT interferometer 12 disposes the end surface of the optical fiber 16 from which the light is emitted at the position conjugate with the position of the anterior segment of the subject eye E, and the anterior segment wavelength swept light source 14 outputs the light with the wavelength suitable for capturing the tomographic image of the anterior segment of the subject eye E. Due to this, the tomographic image capture of the anterior segment of the subject eye E can suitably be executed in the anterior segment OCT measurement of step S14.

Next, the refraction of the subject eye E is measured (reflection measurement) (S16). The reflection measurement is executed by adjusting a scan circle diameter and the irradiation position to the subject eye E based on the tomographic image of the anterior segment of the subject eye E acquired in step S14.

The reflection measurement is executed according to the following procedure. Firstly, the processor 100 adjusts the scanner 40. At this occasion, the processor 100 adjusts the scanner 40 based on the tomographic image of the anterior segment of the subject eye E acquired in step S14. Specifically, the processor 100 calculates a pupil diameter of the subject eye E based on the tomographic image of the anterior segment of the subject eye E acquired in step S14. Then, the processor 100 adjusts the scan circle diameter based on the calculated pupil diameter. That is, the scan circle diameter is set to a value smaller than the pupil diameter. Further, the processor 100 identifies the opaque portion of the crystalline lens of the subject eye E based on the tomographic image of the anterior segment of the subject eye E acquired in step S14. Then, in a case where the opaque portion exists in the crystalline lens of the subject eye E, the processor 100 adjusts the scanner 40 such that the light irradiated to the subject eye E avoids the opaque portion. The scanner 40 is an example of an "irradiation position adjuster".

When the adjustment of the scanner 40 is completed, the processor 100 turns on the reflection measurement light source 82 to collect the image detected by the sensor 98, and measures the refraction by analyzing the image in the processor 100. At this occasion, the refraction is measured under a state in which refractive power adjustment by the crystalline lens of the subject eye E is eliminated by the fogging mechanism that is not shown. Since those used in the well-known ophthalmic apparatuses can be used as the fogging mechanism, detailed description thereof will be omitted.

Figure 11A:
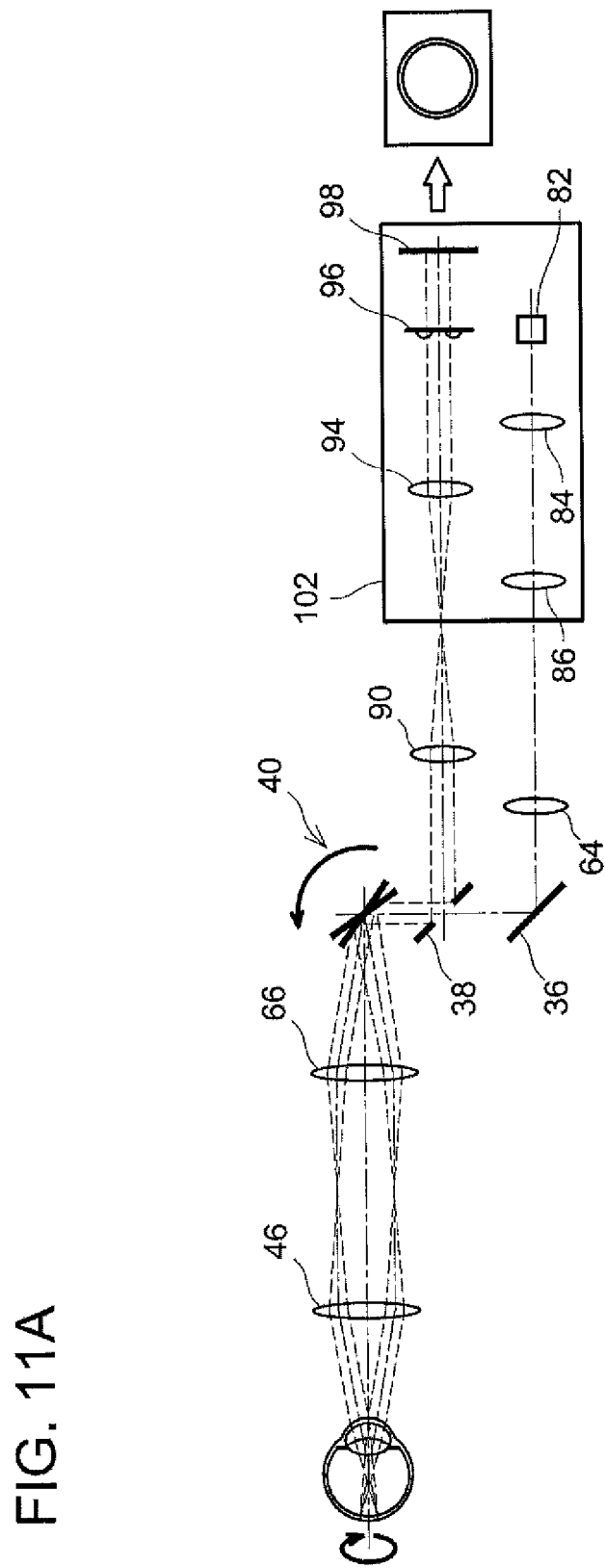
FIGS. 11A to C are diagrams schematically showing an optical path for outputting light from a reflection measurement light source and receiving light reflected from the subjected eye, where 11A shows a case where the subject eye is an emmetropia, 11B shows a case where the subject eye is a myopia, and 11C shows a case where the subject eye is a hypermetropa.
Figure 11B:
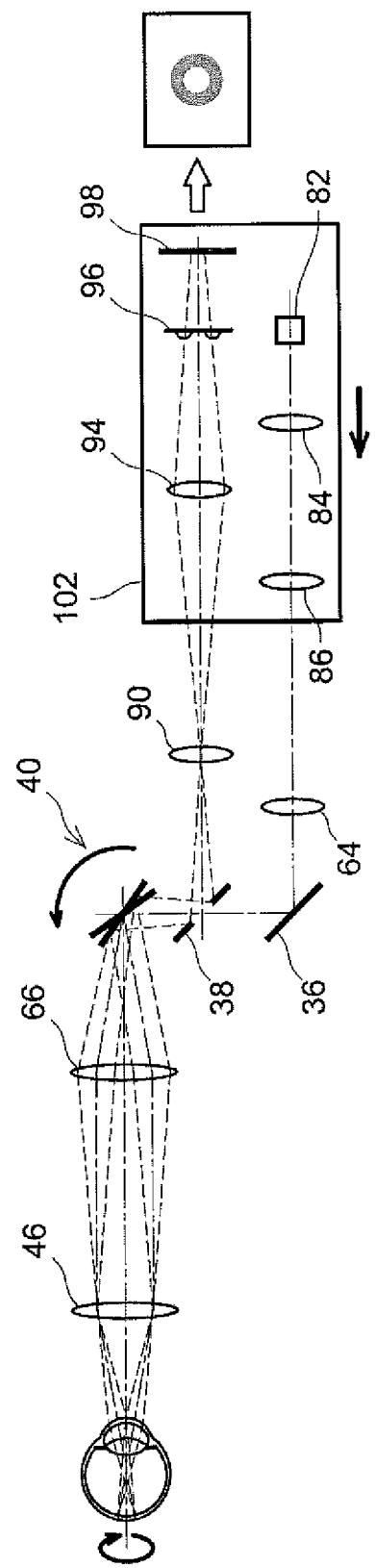
Figure 11C:
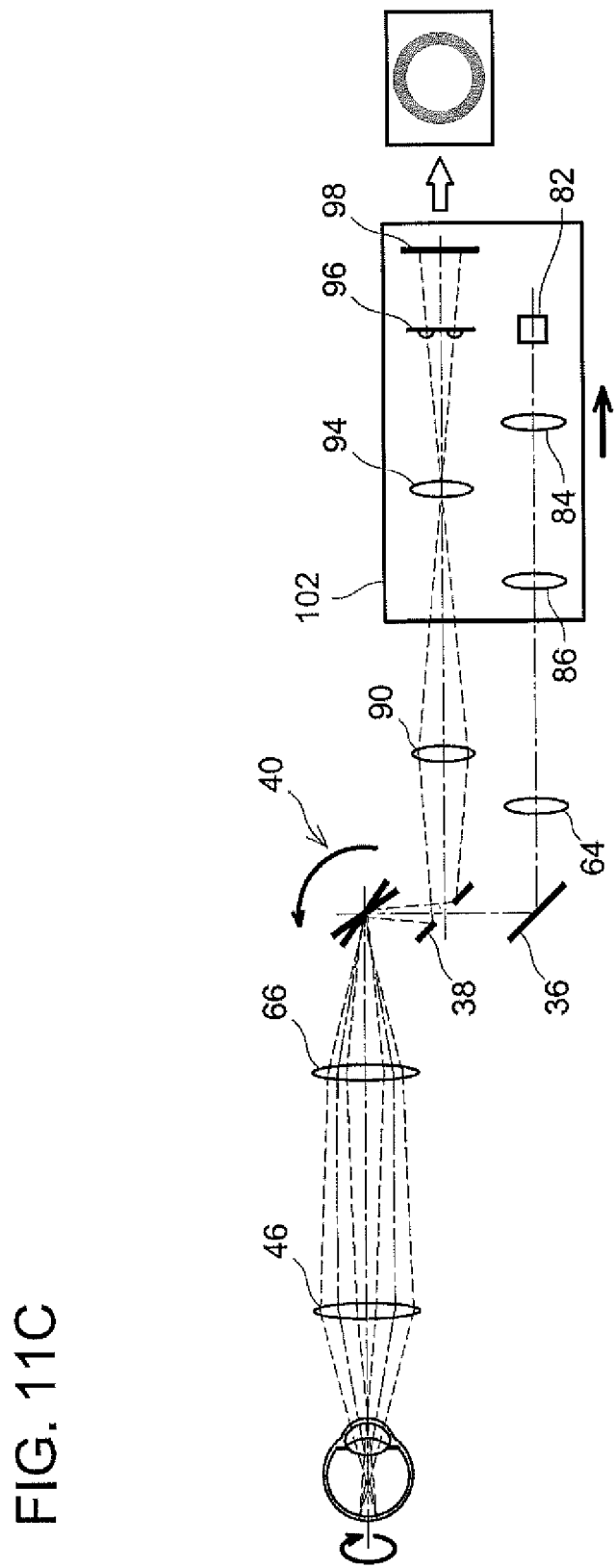

When the reflection measurement is completed, the processor 100 adjusts the focal point adjusting mechanism 102 based on the result of the reflection measurement in step S16 (S18). Here, the adjustment by the focal point adjusting mechanism 102 will be described with reference to FIGS. 11A to C. FIGS. 11A to C show optical paths for projecting the light from the reflection measurement light source 82 and receiving the light reflected from the subject eye E, and only some of optical members disposed on the optical paths (that is, the lenses 64, 66, 84, 86, 90, 94, the dichroic mirror 36, the perforated mirror 38, the scanner 40, the object lens 46, the ring lens 96, and the sensor 98) are shown, and other optical members are omitted from the drawings. Further, FIG. 11A shows a case where the subject eye E is an emmetropia, FIG. 11B shows a case where the subject eye E is a myopia, and FIG. 11C shows a case where the subject eye E is a hypermetropia.

As shown in FIG. 11A, in the case where the subject eye E is an emmetropia, the sensor 98 is disposed at the position conjugate with the position of the retina of the subject eye E, and the image detected by the sensor 98 becomes a thinnest and brightest ring image.

On the other hand, as shown in FIG. 11B, in the case where the subject eye E is a myopia, the image detected by the sensor 98 becomes a thick and blurred ring image due to the refraction being large as compared to the emmetropia. Further, as compared to the case of the emmetropia, a small ring image is obtained. In this case, the focal point adjusting mechanism 102 is actuated to bring the positions of the reflection measurement light source 82 and the sensor 98 closer to the subject eye E and the optical path length of the reflection measurement optical system 80 is thereby shortened. When the sensor 98 moves to the position conjugate with the position of the retina of the subject eye E, the image detected by the sensor 98 becomes a thinnest and brightest ring image.

Further, as shown in FIG. 11C, in the case where the subject eye E is a hypermetropia, the image detected by the sensor 98 becomes a thick and blurred ring image due to the refraction being large as compared to the emmetropia. Further, as compared to the case of the emmetropia, a large ring image is obtained. In this case, the focal point adjusting mechanism 102 is actuated to separate the positions of the reflection measurement light source 82 and the sensor 98 away from the subject eye E and the optical path length of the reflection measurement optical system 80 is thereby lengthened. When the sensor 98 moves to the position conjugate with the position of the retina of the subject eye E, the image detected by the sensor 98 becomes a thinnest and brightest ring image.

When the adjustment by the focal point adjusting mechanism 102 is completed, the processor 100 executes tomographic image capture of the retina of the subject eye E (retinal OCT measurement) (S20). In the retinal OCT measurement, similar procedure as the anterior segment OCT measurement in step S14 is used in that the optical coherence tomography (OCT) method is used. Due to this, points different from the anterior segment OCT measurement in step S14 will be described hereinbelow, and description will be omitted regarding similar points.

Figure 12A:
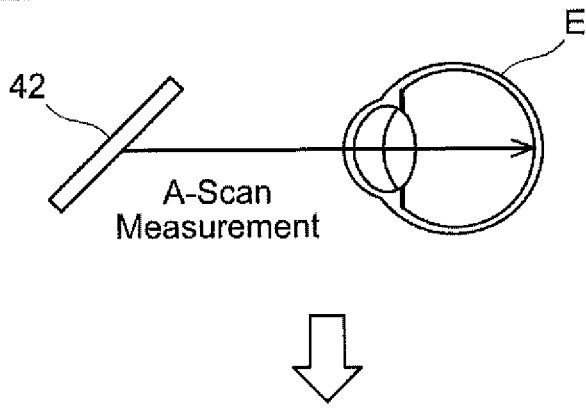
FIGS. 12A to C are diagrams explaining a procedure to process a coherence signal waveform obtained by scanning a wavelength of a retina wavelength swept light source of an eye axial length/retinal OCT optical system.
Figure 12B:
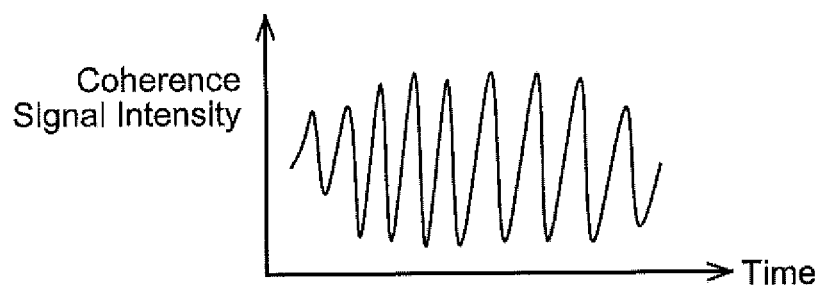
Figure 12C:
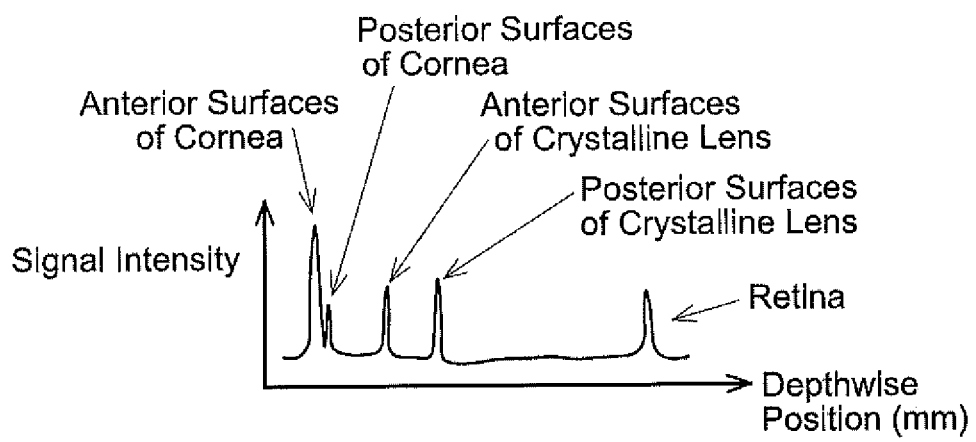

The processor 100 adjusts the scanner 40 in similar procedures as the aforementioned steps S32, S34, and receives the reflected light of the light irradiated from the retina wavelength swept light source 54 using the light receiving element 56. In the eye axial length/retinal OCT optical system 50, the respective optical members are disposed such that the retina wavelength swept light source 54 irradiates the light with the wavelength reaching the retina of the subject eye E and the light irradiated from the retina wavelength swept light source 54 is concentrated at the retina of the subject eye E. Due to this, as shown in FIGS. 12A to C, the processor 100 can identify the positions of the retinal portion of the subject eye E, such as the retina, in addition to the anterior and posterior surfaces of the cornea and the anterior and posterior surfaces of the crystalline lens. This measurement is repeated, similar to the aforementioned step S36, until it is executed for all the preset scan angles.

Figure 13A:
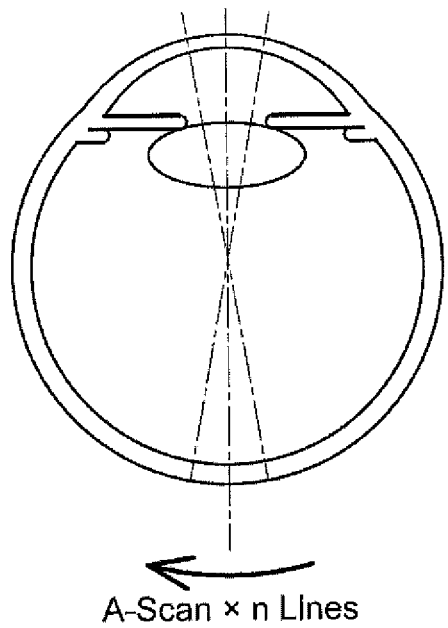
FIGS. 13A, B are diagrams explaining a procedure for identifying a position of each portion of the subject eye from information acquired for each incident position and an incident angle (information acquired from the procedure shown in FIGS. 12A to C) by scanning the incident positions and incident angles of the light to the subject eye within a predetermined range.
Figure 13B:
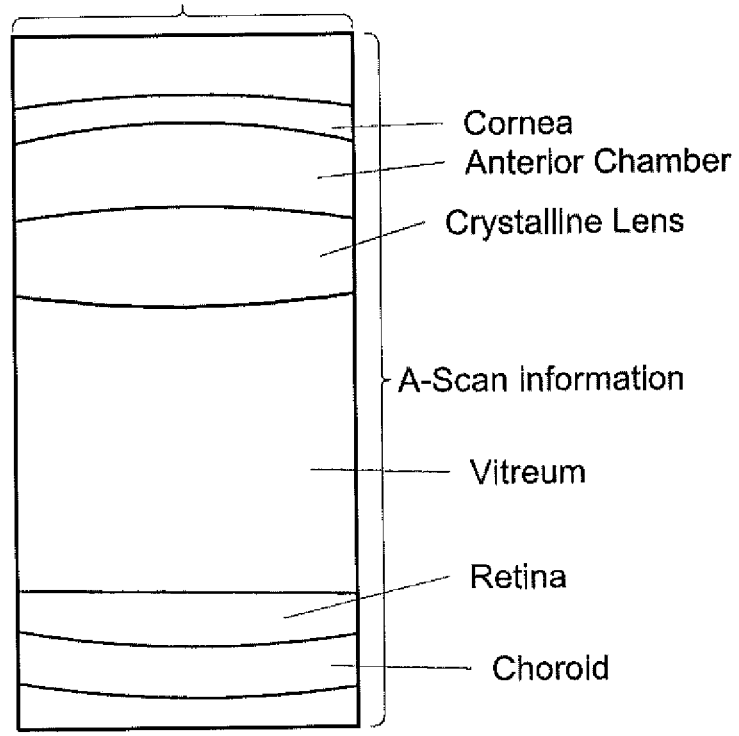

When the measurement is completed for all the scan angles, the processor 100 identifies the positions of the respective portions of the subject eye E from the coherence signals acquired for the respective scan angles similar to step S38. Unlike the anterior segment OCT optical system 10, the eye axial length/retinal OCT optical system 50 executes the pivot scan. Due to this, as shown in FIGS. 13A, B, the two-dimensional information that formed the pivot intraocularly in the subject eye E for each scan angle is obtained. Due to this, the processor 100 identifies the positions of the respective portions of the subject eye E by calculating average values of the positional information of the respective portions of the subject eye E (such as the cornea, the anterior chamber, the crystalline lens, a vitreum, the retina, and the choroid) included in the respective coherence signal information. The shape of the retina of the subject eye E can be calculated and the eye axial length of the subject eye E can be measured from this measurement result.

As aforementioned, the reflection measurement and the retinal OCT measurement execute the measurements by adjusting the scanner 40 based on the measurement result of the anterior segment OCT measurement. Further, the retinal OCT measurement adjusts the irradiation positions of the light to the retina of the subject eye E based on the measurement result of the reflection measurement. As above, highly accurate measurement results can be acquired, and measurement time can be shortened by adjusting measurement conditions of subsequent measurements based on the measurement results from the preceding measurements.

When all the measurements (the anterior segment OCT measurement, the reflection measurement, and the retinal OCT measurement) are completed, the processor 100 outputs an analysis result to the touch panel 104. Since the ophthalmic apparatus 1 of the present embodiment can execute plural types of measurements, namely the anterior segment OCT measurement, the reflection measurement, and the retinal OCT measurement, a state of the subject eye E can be analyzed comprehensively. As the analysis result, for example, the subject eye measurements may be executed before a cataract surgery to obtain IOL power calculation, cornea aberration, and opaque state of the crystalline lens. Further, by executing the subject eye measurements before the cataract surgery, errors relative to the postoperative refraction of the subject eye E as predicted preoperatively can be evaluated, and this can be used to improve accuracy of the IOL power calculation. Further, by executing the measurements on a subject eye suffering glaucoma, progression of the glaucoma can be predicted from a retina thickness distribution, and closure angles thereof may be screened. Further, by executing the measurement of an excessively-myopia subject, the state of the subject eye can be examined in detail and comprehensively.

The ophthalmic apparatus 1 of the present embodiment can execute plural types of measurements such as the anterior segment OCT, the retinal OCT, the eye axial length, and the refraction by a single apparatus, and each of the measurements can be executed highly accurately. Although ophthalmic apparatuses capable of executing plural types of measurements in a single apparatus had been developed in the past, an apparatus that can accurately measure all of the anterior segment OCT, the retinal OCT, the eye axial length, and the refraction has not yet been developed. For example, the aforementioned ophthalmic apparatus of Japanese Patent Application Publication No. 2016-77774 is configured capable of measuring the cornea shape, the refraction, the eye axial length, and the like of the subject eye. However, since the cornea shape is measured by using the kerato measurement ring, it is capable of measuring the shape of the anterior surface of the cornea, however, it cannot measure other portions of the anterior segment such as the posterior surface of the cornea and the crystalline lens. Further, the ophthalmic apparatus of Japanese Patent Application Publication No. 2016-77774 does not have the mechanism for measuring the retina. Moreover, the ophthalmic apparatus of Japanese Patent Application Publication No. 2017-502817 is configured capable of measuring the anterior segment and the retina. However, since it splits light outputted from a single light source into two light beams with difference wavelengths, its collectable rate of the reflected light from a target portion of the subject eye is thereby deteriorated. Due to this, both the anterior segment and the retina cannot be measured accurately. Further, the ophthalmic apparatus of Japanese Patent Application Publication No. 2017-502817 does not have the mechanism for measuring the refraction. The ophthalmic apparatus 1 of the present embodiment has different wavelengths for the light to be irradiated to the anterior segment and the light to be irradiated to the retina, and thus the light with the respectively-suitable wavelengths can be irradiated. Due to this, all of the plural types of measurements can be executed with high accuracy.

Further, in the ophthalmic apparatus 1 of the present embodiment, the scanner 40 is used for all of the plural types of measurements. Due to this, the configurations of the optical systems in the ophthalmic apparatus 1 can be suppressed from becoming complicated, and the number of components can be reduced. Further, since a relatively expensive scanner such as the galvanometer is generally not used for the reflection measurement, it becomes difficult to accurately measure the refraction of the subject eye. In the ophthalmic apparatus 1 of the present embodiment, the scanner 40 is shared among all of the measurements, and plural scanners for respective types of measurements are not provided. Due to this, the scanner with the high performance is used for all of the measurements, and thus all of the plural types of measurements can be executed highly accurately.

Second Embodiment

Figure 14:
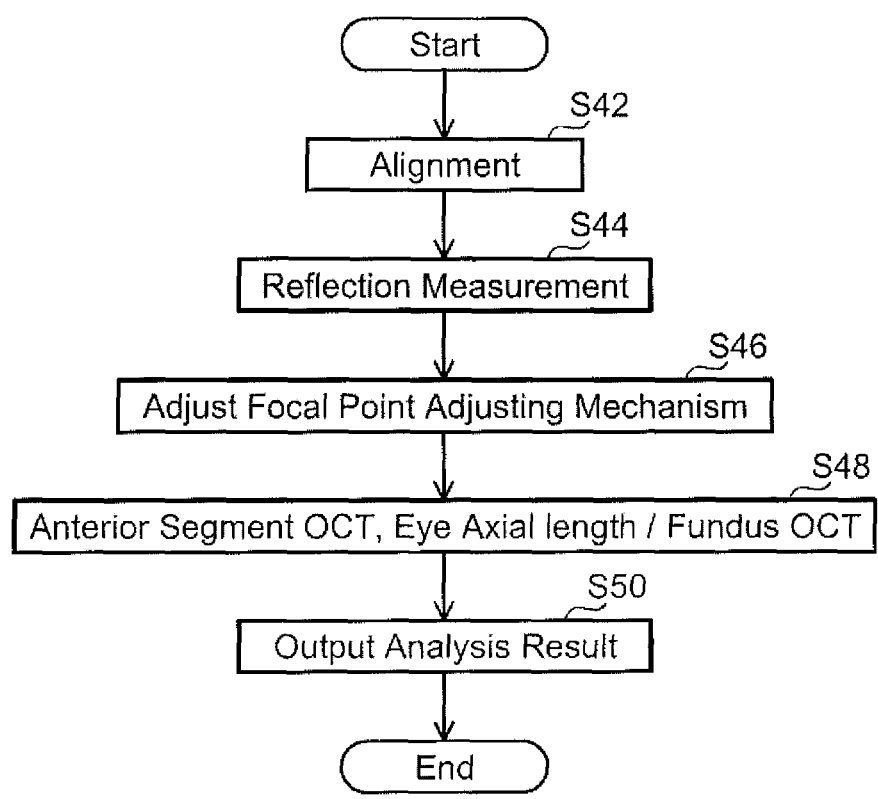
FIG. 14 is a flowchart showing an example of a procedure for plural types of measurement processes executed in an ophthalmic apparatus of a second embodiment.

In the above first embodiment, the reflection measurement and the retinal OCT measurement are executed after having executed the anterior segment OCT measurement, however, an order by which the anterior segment OCT measurement, the reflection measurement, and the retinal OCT measurement are executed is not particularly limited. Hereinbelow, an example that executes the anterior segment OCT measurement, the reflection measurement, and the retinal OCT measurement in an order different from that of the first embodiment will be described. FIG. 14 is a flow chart showing an example of a process for executing plural types of measurements on the subject eye E using the ophthalmic apparatus 1. As shown in FIG. 14, firstly the alignment of the subject eye E and the ophthalmic apparatus 1 is executed (S42). Since the alignment in step S42 is same step as step S12 of the first embodiment, detailed description thereof will be omitted.

When the alignment is completed, the reflection measurement is executed (S44). The reflection measurement in step S44 differs from step S16 of the first embodiment in that it does not adjust the scanner 40 based on the measurement result of the anterior segment OCT measurement, however, other procedures thereof are similar step as that of step S16, so detailed description thereof will be omitted. In this embodiment, since the anterior segment OCT measurement is not executed prior to the reflection measurement, the scanner 40 cannot be adjusted based on the measurement result of the anterior segment OCT measurement. Thus, the reflection measurement is executed based on a setting that is set to the processor 100 (initial setting). The reflection measurement may be executed by adjusting the scanner 40 based on measurement results from the reflection measurement executed on the subject eye E in the past.

When the reflection measurement is completed, the processor 100 adjusts the focal point adjusting mechanism 102 based on the result of the reflection measurement in step S44 (S46). The adjustment of the focal point adjusting mechanism 102 in step S46 is same step as step S18 of the first embodiment, so detailed description thereof will be omitted. As aforementioned, the focal point adjusting mechanism 102 integrally moves the lens 58 of the eye axial length/retinal OCT optical system 50 together with the optical members of the reflection measurement optical system 80. Due to this, by executing step S44, the light irradiated from the retina wavelength swept light source 54 of the eye axial length/retinal OCT optical system 50 can be concentrated at the retina of the subject eye E.

When the adjustment by the focal point adjusting mechanism 102 is completed, the processor 100 simultaneously executes the anterior segment OCT measurement and the retinal OCT measurement (S48). The light irradiated from the retina wavelength swept light source 54 of the eye axial length/retinal OCT optical system 50 has been adjusted to be concentrated at the retina of the subject eye E in step S46. Due to this, the retinal OCT measurement can be executed accurately. Thus, even if the anterior segment OCT measurement and the retinal OCT measurement are executed simultaneously, each of the anterior segment OCT measurement and the retinal OCT measurement can be measured accurately. The anterior segment OCT measurement in step S48 is same step as step S14 of the first embodiment, and the retinal OCT measurement in step S48 is same step as step S20 of the first embodiment, so detailed descriptions thereof will be omitted.

In this embodiment, the reflection measurement and the adjustment by the focal point adjusting mechanism 102 are executed first. Due to this, the retinal OCT measurement can be executed accurately. Further, the ophthalmic apparatus 1 of the first embodiment uses the same scanner 40 for both the anterior segment OCT measurement and the retinal OCT measurement. Due to this, the anterior segment OCT measurement and the retinal OCT measurement can be executed simultaneously by executing the reflection measurement and the adjustment by the focal point adjusting mechanism 102 first, so the measurement time can be shortened.

Third Embodiment

Figure 15:
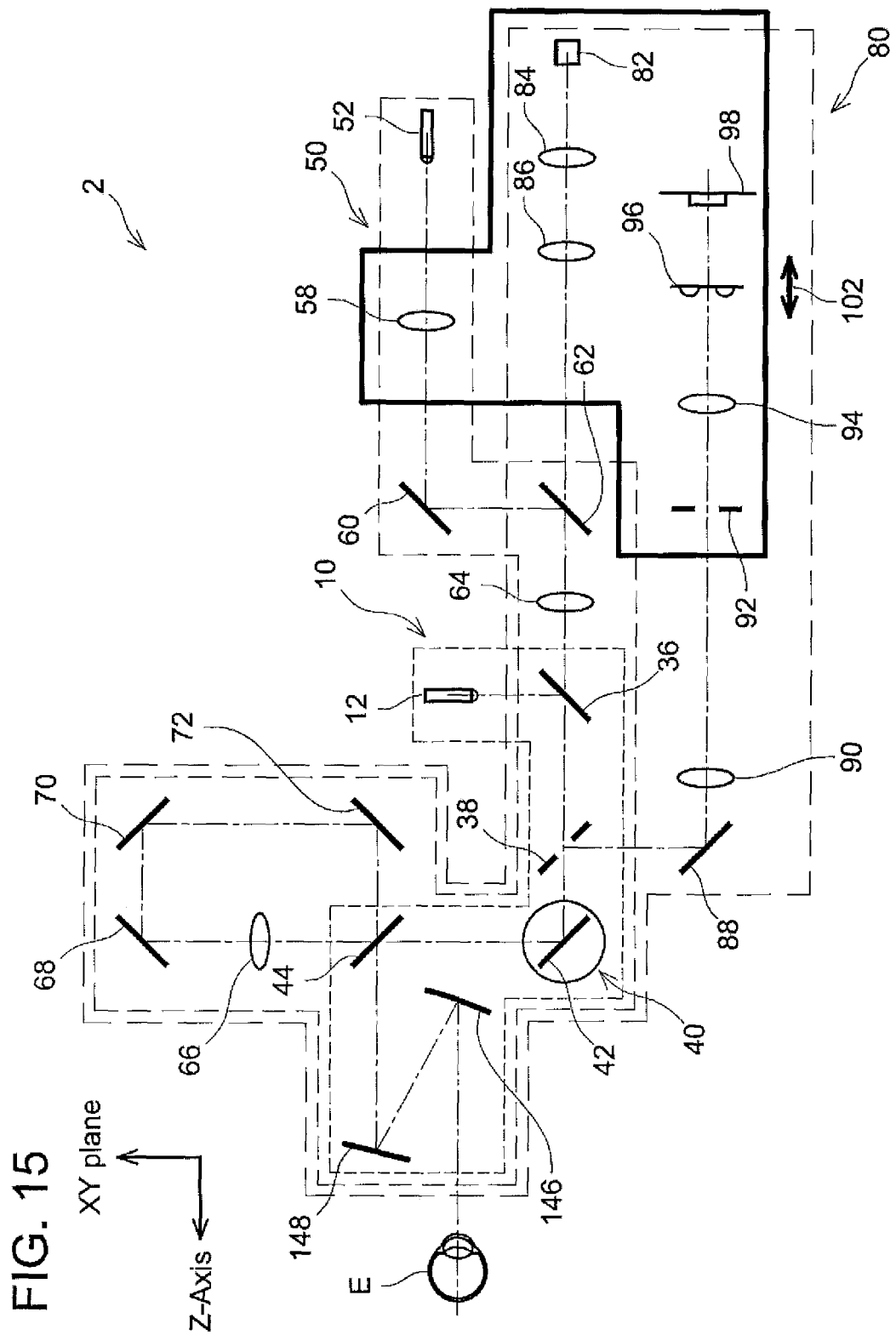
FIG. 15 shows a schematic configuration of an optical system of an ophthalmic apparatus of a third embodiment.

In the aforementioned first and second embodiments, the object lens 46 is disposed between the dichroic mirror 44 and the subject eye E, however, no limitation is made to this configuration. For example, as shown in FIG. 15, a mirror 148 and a curved mirror 146 may be disposed between the dichroic mirror 44 and the subject eye E. An ophthalmic apparatus 2 of the present embodiment differs from the ophthalmic apparatuses 1 as aforementioned in that it disposes the mirror 148 and the curved mirror 146 between the dichroic mirror 44 and the subject eye E, but other configurations are substantially same. Thus, the configurations similar to those of the aforementioned ophthalmic apparatuses 1 will be omitted of detailed description therefor.

For example, a nonaxial parabolic mirror, or a spherical mirror may be used as the curved mirror 146. For all of the anterior segment OCT optical system 10, the eye axial length/retinal OCT optical system 50, and the reflection measurement optical system 80, the light irradiated from the light source is irradiated parallel to the optical axis upon when it is irradiated from the dichroic mirror 44 toward the subject eye E. The light irradiated from the dichroic mirror 44 is reflected by the mirror 148 and the curved mirror 146 in this order, and the light reflected on the curved mirror 146 is irradiated to the subject eye E. By configuring to dispose the mirror 148 and the curved mirror 146 between the dichroic mirror 44 and the subject eye E and to irradiate the light irradiated from the curved mirror 146 to the subject eye E, color aberration caused by differences in the wavelengths of the light (measurement light) irradiated to the subject eye E can be suppressed from occurring. Due to this, images with a greater image quality can be acquired by the anterior segment OCT measurement, the retinal OCT measurement, and the reflection measurement.

Fourth Embodiment

Figure 16:
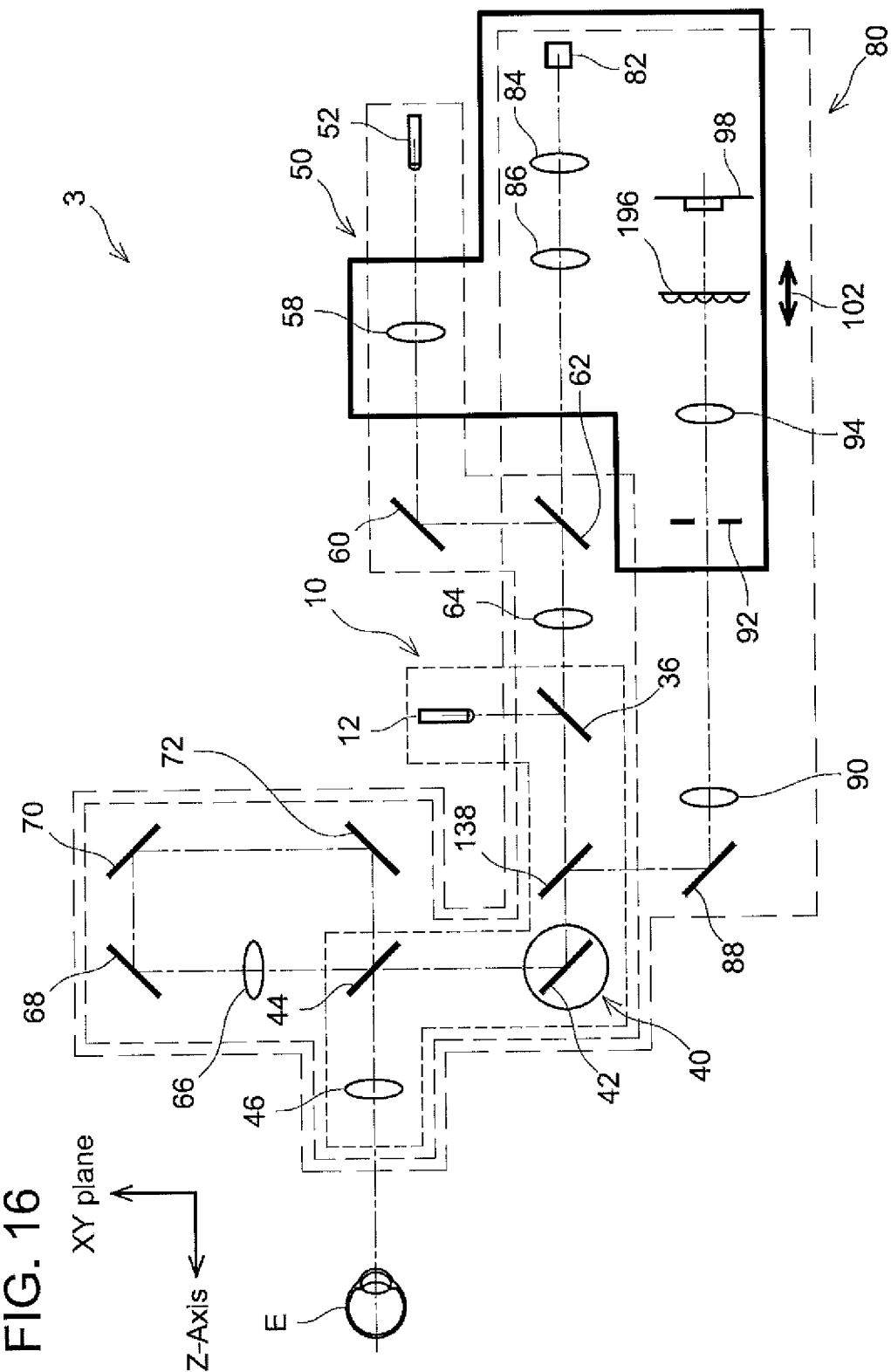
FIG. 16 shows a schematic configuration of an optical system of an ophthalmic apparatus of a fourth embodiment.

In the aforementioned first to third embodiments, the perforated mirror 38 is disposed between the dichroic mirror 36 and the scanner 40 and the ring lens 96 is disposed between the lens 94 and the sensor 98, however, no limitation is made to this configuration. For example, as shown in FIG. 16, a half mirror 138 may be disposed between the dichroic mirror 36 and the scanner 40, and a lens array 196 may be disposed between the lens 94 and the sensor 98. An ophthalmic apparatus 3 of the present embodiment differs from the ophthalmic apparatuses 1 as aforementioned in that it disposes the half mirror 138 between the dichroic mirror 36 and the scanner 40 and the lens array 196 between the lens 94 and the sensor 98, but other configurations are substantially same. Thus, the configurations similar to those of the aforementioned ophthalmic apparatuses 1 will be omitted of detailed description therefor.

In this embodiment, in the reflection measurement optical system 80, the reflected light from the subject eye E is irradiated to the half mirror 138 through the object lens 46, the dichroic mirror 44, the mirrors 72, 70, 68, the lens 66, the dichroic mirror 44, and the scanner 40. The light irradiated to the half mirror 138 is split, and substantially a half thereof is reflected on the half mirror 138. The light reflected on the half mirror 138 is irradiated to the lens array 196 through the mirror 88, the lens 90, the aperture 92, and the lens 94. The lens array 196 includes numerous small lenses, and these numerous small lenses are arranged in a matrix pattern on the lens 94 side. When the light is irradiated to the lens array 196, light at a same number as the number of the numerous small lenses is irradiated from the lens array 196 to the sensor 98. When the light including distorted wave fronts is irradiated to the lens array 196, light in a state of having a displaced optical axis is irradiated to the sensor 98 from a lens among the numerous small lenses at a position corresponding to a position of the distortion. That is, by disposing the lens array 196 between the lens 94 and the sensor 98, same function as an optical system for a wave front sensor can be given to the reflection measurement optical system 80. Due to this, the reflection measurement optical system 80 can measure not only the entire refraction of the subject eye E, but also the entire aberration of the subject eye E, so information related to optical refraction of the subject eye E can be measured in further detail.

While specific examples of the present disclosure have been described above in detail, these examples are merely illustrative and place no limitation on the scope of the patent claims. The technology described in the patent claims also encompasses various changes and modifications to the specific examples described above. Further, the technical elements explained in the present description or drawings provide technical utility either independently or through various combinations, and are not limited to the combinations described at the time the claims are filed.

What is claimed is:

1. An ophthalmic apparatus comprising:
   a first light source configured to output first light to be irradiated to an anterior segment of a subject eye;
   a second light source configured to output second light to be irradiated to a retina of the subject eye,
   a mirror disposed on a first optical path and on a second optical path, the first optical path being an optical path of the first light irradiated from the first light source to the anterior segment of the subject eye and the second optical path being an optical path of the second light irradiated from the second light source to the retina of the subject eye; and
   a scanner disposed on the first optical path and on the second optical path,
   wherein the apparatus is configured capable of executing a first examination using the first light reflected from the anterior segment and a second examination using the second light reflected from the retina,
   a wavelength of the second light outputted from the second light source is smaller than a wavelength of the first light outputted from the first light source,
   the scanner is configured to scan the first light outputted from the first light source and to scan the second light outputted from the second light source, and
   the scanner is disposed on the optical path from the first light source to the mirror and on the optical path from the second light source to the mirror.

2. The ophthalmic apparatus according to claim 1, wherein
   the wavelength of the first light outputted from the first light source is 0.95 μm or more and 1.80 μm or less, and
   the wavelength of the second light outputted from the second light source is 0.4 μm or more and 1.15 μm or less.

3. The ophthalmic apparatus according to claim 1,
   wherein the mirror is configured to reflect the first light from the first light source and transmit the second light from the second light source.

4. The ophthalmic apparatus according to claim 3, wherein
   the first optical path includes a first optical path section being a optical path of the first light irradiated from the mirror to the subject eye, and
   the second optical path includes the first optical path section.

5. The ophthalmic apparatus according to claim 1, wherein
   the scanner is configured capable of changing an incident position of the second light outputted from the second light source on the subject eye and an incident angle of the second light relative to the subject eye, and
   when the second light outputted from the second light source is to be scanned by the scanner, scan is executed such that optical paths of the scanned light entering the subject eye intersect each other between the retina and a crystalline lens of the subject eye.

6. The ophthalmic apparatus according to claim 1, further comprising:
a lens disposed between the mirror and the subject eye,
wherein the scanner is configured capable of changing an incident position of the first light outputted from the first light source on the subject eye, and
when the first light outputted from the first light source is to be scanned by the scanner, scan is executed such that the progressing directions of the light entering the subject eye are parallel to an optical axis of the lens.

7. The ophthalmic apparatus according to claim 1, further comprising:
a third light source configured to output third light for measuring ocular refraction of the subject eye,
wherein a third optical path being an optical path of the third light outputted from the third light source merges with an optical path section of the second optical path, the optical path section being a section from the second light source to the scanner, and
the third light outputted from the third light source passes through the second optical path and is irradiated to the retina of the subject eye.

8. The ophthalmic apparatus according to claim 1, further comprising:
a processor configured to calculate a shape of the anterior segment of the subject eye based on reflected light of the first light reflected from the anterior segment of the subject eye and to calculate a shape of the retina of the subject eye and an eye axial length of the subject eye based on reflected light of the second light reflected from the retina of the subject eye.

* * * * *